United States Patent
Wangerin et al.

(10) Patent No.: US 8,466,420 B2
(45) Date of Patent: Jun. 18, 2013

(54) CHARGE LOSS CORRECTION

(75) Inventors: Kristen Ann Wangerin, Watervliet, NY (US); Wen Li, Clifton Park, NY (US); Yanfeng Du, Rexford, NY (US); Floribertus Heukensfeldt Jansen, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 18 days.

(21) Appl. No.: 12/794,525

(22) Filed: Jun. 4, 2010

(65) Prior Publication Data
US 2011/0297838 A1 Dec. 8, 2011

(51) Int. Cl.
*G01T 1/161* (2006.01)

(52) U.S. Cl.
USPC ............ 250/363.09; 250/363.07; 250/363.06; 250/363.03

(58) Field of Classification Search
USPC ..................................... 250/363.09
See application file for complete search history.

(56) References Cited

U.S. PATENT DOCUMENTS

| | | | | |
|---|---|---|---|---|
| 6,046,454 A | * | 4/2000 | Lingren et al. | 250/370.01 |
| 6,329,658 B1 | | 12/2001 | Mestais et al. | |
| 6,987,833 B2 | | 1/2006 | Du et al. | |
| 7,208,739 B1 | * | 4/2007 | Yanoff et al. | 250/363.09 |
| 7,263,167 B2 | | 8/2007 | Walter et al. | |
| 2004/0227091 A1 | | 11/2004 | LeBlanc et al. | |
| 2006/0058685 A1 | | 3/2006 | Fomitchov et al. | |
| 2006/0243916 A1 | | 11/2006 | Sergent et al. | |
| 2006/0289777 A1 | | 12/2006 | Li et al. | |
| 2007/0076842 A1 | | 4/2007 | Tkaczyk et al. | |
| 2007/0167697 A1 | | 7/2007 | Avila et al. | |
| 2009/0321730 A1 | | 12/2009 | Lynn et al. | |
| 2011/0155918 A1 | * | 6/2011 | Bouhnik et al. | 250/370.14 |

FOREIGN PATENT DOCUMENTS

| CA | 2185091 A1 | 3/1997 |
|---|---|---|
| WO | 2009092165 A1 | 7/2009 |

* cited by examiner

*Primary Examiner* — Christine Sung
(74) *Attorney, Agent, or Firm* — Marie-Claire B. Maple

(57) ABSTRACT

The present disclosure relates to the correction of charge loss in a radiation detector. In one embodiment, correction factors for charge loss may be determined based on depth of interaction and lateral position within a radiation detector of a charge creating event. The correction factors may be applied to subsequently measured signals to correct for the occurrence of charge loss in the measured signals.

20 Claims, 22 Drawing Sheets

CHARGE LOSS CORRECTION

BACKGROUND OF THE INVENTION

The subject matter disclosed herein relates to radiation detection techniques and systems and, more particularly, to the detection and correction of signals using such systems.

In single photon emission computed tomography (SPECT) imaging and positron emission tomography (PET) imaging, a radiopharmaceutical is administered to a patient. The radiopharmaceutical is typically selected so as to be preferentially or differentially distributed in the body based on the physiological or biochemical processes in the body. For example, a radiopharmaceutical may be selected that is preferentially processed or taken up by tumor tissue. In such an example, the radiopharmaceutical will typically be disposed in greater concentrations around tumor tissue within the patient.

In SPECT and PET imaging, gamma rays are generated when the radiopharmaceutical breaks down or decays within the patient. These gamma rays interact with detection mechanisms within the respective PET or SPECT scanner, which allow the decay events to be localized, thereby providing a view of where the radiopharmaceutical is distributed throughout the patient. In this manner, a caregiver can visualize where in the patient the radiopharmaceutical is disproportionately distributed and may thereby identify where physiological structures and/or biochemical processes of diagnostic significance are located within the patient.

The mechanism used to detect the gamma rays may include a conversion material which, when impacted by the gamma rays, generates an electrical charge that may be detected by electrodes proximate to the conversion material. The detected charges, which provide information about the location, energy, and timing of the gamma ray impact events, may in turn be used to generate images of the patient or other object undergoing imaging.

However, due to structural considerations related to the detector, in certain circumstances charge information may be lost. For example, due to the segregation of a detector into various unit areas of measurement or read-out, e.g., pixels, gamma ray impacts that occur generally between two or more pixels may go undetected or may otherwise undergo loss of some of the charge information that would otherwise contribute to the imaging process. Loss of this charge information may result in reduced or degraded performance of the imaging system.

BRIEF DESCRIPTION OF THE INVENTION

In one embodiment, a method for correcting for charge losses in a radiation detector is provided. In accordance with this method, one or more anode signals and a cathode signal are acquired from the radiation detector. The one or more anode signals and cathode signal arise in response to a gamma ray interaction with the radiation detector. A depth of interaction is determined for the gamma ray interaction with the radiation detector. A lateral position of the gamma ray interaction with respect to the one or more anodes is determined. The one or more anode signals are sorted into one of a plurality of spectra based on the depth of interaction and lateral position. A correction factor is determined based on the difference between the one or more anode signals and expected values for the one or more anode signals.

In a further embodiment, a method for determining a degree of signal loss at a radiation detector is provided. In accordance with this method, a first subset of detected events in which radiation has interacted within a depth range less than the thickness of the radiation detector is determined. A second subset of the detected events corresponding to lateral positions of the detected events within the radiation detector is also determined. A count profile for the frequency of occurrence of sums of a set of anode signals associated with the detected events is generated. In addition, based on the count profile, a fraction of signal lost for particular values of depth of interaction and lateral position is determined.

In an additional embodiment, an imaging system is provided. The imaging system includes a radiation detector. The radiation detector includes a direct conversion material, one or more cathode electrodes disposed on a first surface of the direct conversion material, and a plurality of anode electrodes disposed on a second surface of the direct conversion material. The imaging system also includes data acquisition circuitry in communication with the one or more cathode electrodes and the plurality of anode electrodes and signal processing circuitry in communication with the data acquisition circuitry. The imaging system also includes an operator workstation configured to control the operation of and to communicate with one or both of the data acquisition circuitry and the signal processing circuitry. One or more of the data acquisition circuitry, the signal processing circuitry, or the operator workstation is configured to execute code which, when executed, performs the following: processes a measured set of signal data, accesses one or more correction factors suitable for correcting for charge loss as a result of being split between two or more of the anode electrodes or of being lost to a gap separating respective anode electrodes, and applies the one or more correction factors to the measured set of signal data to generate a corrected set of signal data corrected for the charge loss.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

In accordance with the present disclosure, signal data is acquired using an imaging or isotope detection modality, such as a single photon emission computed tomography (SPECT) or positron emission tomography (PET) imaging system, or another suitable imaging modality. In one embodiment, a radiation detector, such as a cadmium zinc telluride (CZT) detector, converts incident radiation to electrical signals, which may be used to generate images. In such an embodiment, when a gamma ray interacts with the CZT material, electron-hole pairs are generated which move toward the electrodes associated with the CZT material. In one implementation, the anode structure may be formed as grid of separated anode electrodes (i.e., pixels) on which the moving electrons and holes induce charge. In normal operation, the induced charge on the anode electrodes is proportional to the incident gamma energy. Therefore, by measuring the induced charge, the incident gamma energy can be indirectly measured. Depending on the site of gamma ray interaction and the shape and size of the anode electrodes, some of the charge may not be sensed at the respective anode electrodes. The distance of the event to the anode electrode is a strong effect since the amount of charge induced on the anode by the holes is a function of distance. Additionally, electrons may move toward the gap between anode electrodes instead of toward one of the anode electrodes itself. As a result of such charge loss, the sensed charge may represent less signal than the actual deposited energy. As discussed herein, the present disclosure addresses corrections for such charge loss.

Figure 1:
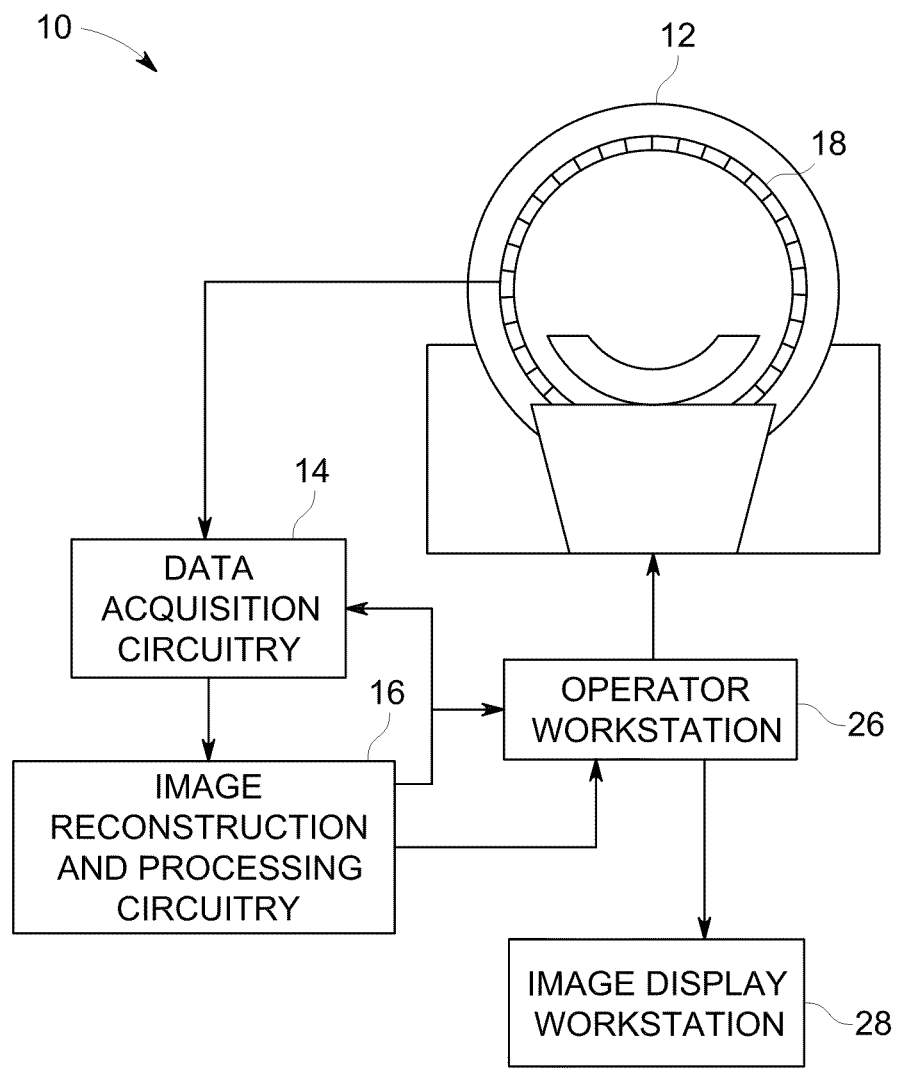
FIG. 1 is a diagrammatical representation of a SPECT imaging system in accordance with aspects of the present disclosure.

With the foregoing in mind and turning now to the drawings, FIG. 1 depicts a SPECT system 10 operating in accordance with certain aspects of the present disclosure. As will be appreciated, in other implementations the imaging system may correspond to another type of suitable imaging modality, such as a PET imaging system. The SPECT imaging system of FIG. 1 is merely depicted and discussed to facilitate explanation of the presently disclosed signal processing approach in a particular context so that aspects of the approach may be more readily understood.

Returning now to FIG. 1, the depicted SPECT system 10 includes a detector assembly 12, data acquisition circuitry 14, and image reconstruction and processing circuitry 16. The detector assembly 12 of the SPECT system 10 typically includes a number of detector modules (generally designated by reference numeral 18) arranged in one or more rings, as depicted in FIG. 1. In certain embodiments a collimator assembly may also be associated with the detector assembly 12 to facilitate localization of gamma ray impacts. The depicted SPECT system 10 also includes an operator workstation 26 and an image display workstation 28.

To facilitate explanation and discussion of the operation of the SPECT system 10, the detector acquisition circuitry 14, and the image reconstruction and processing circuitry 16 are shown separately from other illustrated components (e.g., the detector assembly 12, the operator workstation 26, and the image display workstation 28). However, in certain implementations, some or all of these circuitries may be provided as part of the detector assembly 12, the operator workstation 26, and/or the image display workstation 28. For example, the hardware, software, and/or firmware executed on or provided as part of the image reconstruction and processing circuitry 16, whether provided as part of the detector assembly 12, the operator workstation 26, and/or the image display workstation 28, may be used to perform various image processing actions described herein. In certain implementations the image reconstruction and processing circuitry 16 may include specially programmed hardware, memory, or processors (e.g., application-specific integrated circuits (ASICs)) for performing data processing steps to compensate for charge loss at the detector, as discussed herein. Similarly, all or part of these charge loss correction steps may be performed using one or more general or special purpose processors and stored code or algorithms configured to execute on such processors. Likewise, a combination of special purpose hardware and/or circuitry may be used in conjunction with one or more processors configured to execute stored code to implement the steps discussed herein. The results of such data processing steps may be displayed on one or both of the operator workstation 26 or a separate image display workstation 28, if present.

Keeping in mind the example of the SPECT system 10 discussed above, or the corresponding components of other types of suitable imaging systems, a brief description of the functioning of one such system is provided to facilitate further explanation of the present approach. In particular, SPECT imaging is primarily used to measure metabolic activities that occur in tissues and organs and, in particular, to localize aberrant metabolic activity. In SPECT imaging, the patient is typically injected with a solution that contains a radioactive tracer. The solution is distributed and absorbed throughout the body in different degrees, depending on the tracer employed and the functioning of the organs and tissues.

In particular, the radioactive tracer emits positrons that interact with surrounding particles, thereby generating gamma rays. In a SPECT imaging system 10, the gamma rays are detected by the detector assembly 12. The gamma rays may be collimated so that the detection of a gamma ray may be used to determine the line of response along which the gamma ray traveled before impacting the detector, allowing localization of the annihilation event to that line. By detecting a number of such gamma rays, and calculating the corresponding lines traveled by the gamma rays, the concentration of the radioactive tracer in different parts of the body may be estimated and a tumor, thereby, may be detected. Therefore, accurate detection and localization of the gamma rays forms a fundamental and foremost objective of the SPECT system 10.

In view of these comments, and returning now to FIG. 1, the detector acquisition circuitry 14 is adapted to read out signals generated in response to the gamma rays from the detector modules 18 of the detector assembly 12. The signals acquired by the detector acquisition circuitry 14 are provided to the image reconstruction and processing circuitry 16. The image reconstruction and processing circuitry generates an image based on the derived gamma ray emission locations. The operator workstation 20 is utilized by a system operator to provide control instructions to some or all of the described components and for configuring the various operating parameters that aid in data acquisition and image generation. The operating workstation 20 may also display the generated image. Alternatively, the generated image may be displayed at a remote viewing workstation, such as the image display workstation 22.

Figure 2:
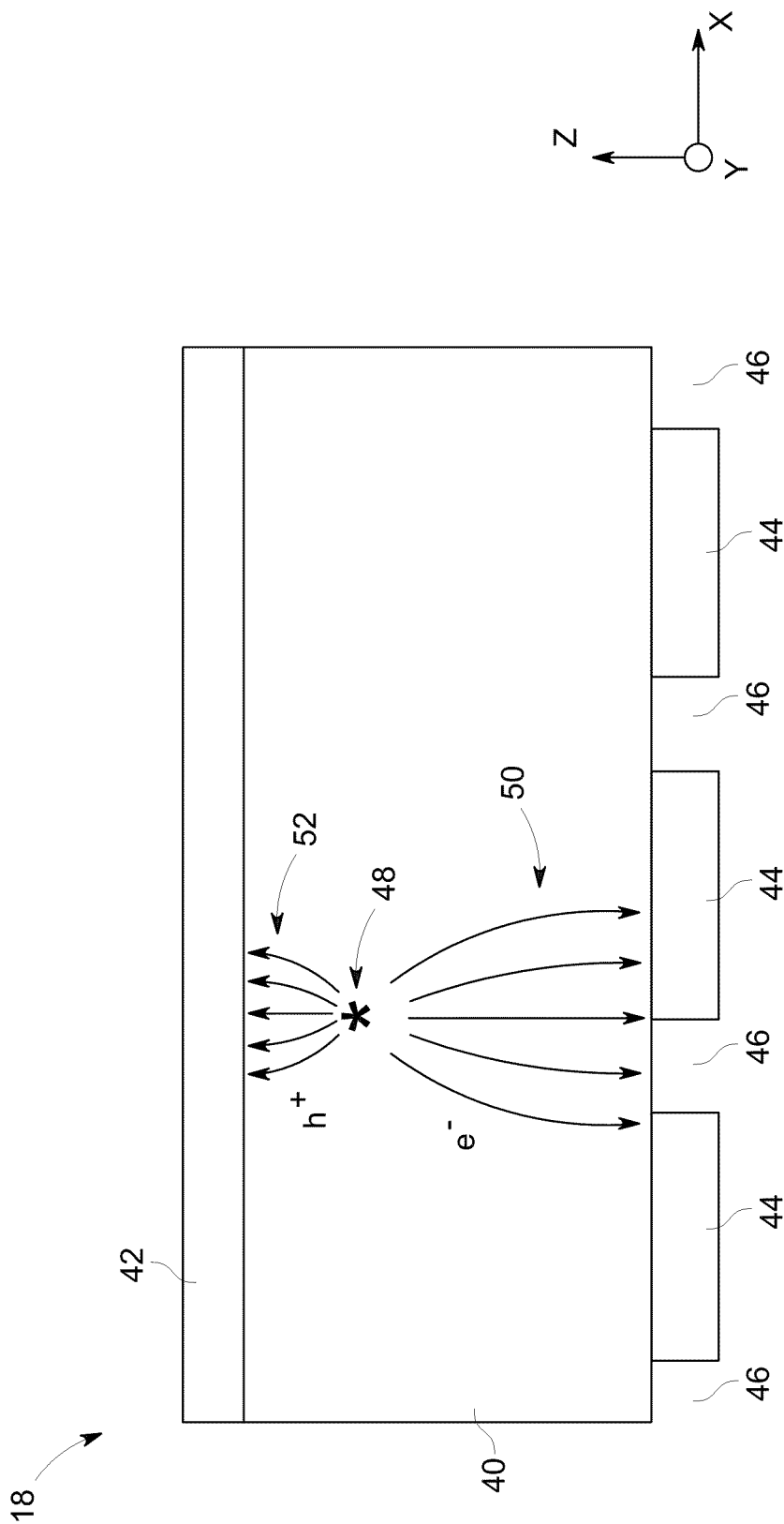
FIG. 2 is a cross-sectional view of a portion of a detector module in accordance with aspects of the present disclosure.

With the foregoing in mind, FIG. 2, depicts a cut-away view of a portion of a detector module 18 that includes a direct conversion material 40, such as a CZT crystal, bracketed by a cathode electrode 42 and a set of anode electrodes 44, which define pixels of the detector assembly 12. As will be appreciated, in a detector assembly 18, the anode electrodes 44 may be provided as a grid or array that includes hundreds, thousand, or tens of thousands of anodes electrodes 44 arranged laterally in two dimensions (e.g., the x and y-dimensions). Conversely, the cathode electrode 42 may be formed as a singular or common electrode spaced apart from the anode electrodes 44 in the z-dimension, i.e., on the opposite facing of the direct conversion material 40. As will be appreciated, gaps 46 may separate the anodes electrodes 44 of a detector module 18. In one embodiment, the anode electrodes 44 are approximately 1.86 mm in both the length and width dimensions while the corresponding gap 46 separating the respective anode electrodes 44 is approximately 0.6 mm wide. The gaps 46 may be filled (such as with a high resistivity material) or may be empty. Regardless of their composition, the gaps 46 are electrically separate and distinct from the anode electrodes 44 they define.

In addition, FIG. 2 depicts an example of a conversion event 48 in which a gamma ray impacts a region within the direct conversion material 40, thereby generating electron-hole pairs. Subsequent to such a conversion event 48, the electrons 50 may migrate toward the anode electrodes 44 while the holes 52 migrate toward the cathode electrode 42. As will be appreciated, depending on the depth within the direct conversion material 40 of the conversion event 48 and/or the lateral positioning of the conversion event 48 relative to the underlying anode electrodes 44, the generated electrons 50 may all migrate to a single anode electrode 44 or may be split between two or more anode electrodes 44. Further, depending on the depth and lateral positioning of the conversion event 48, some portion of the electrons 50 may migrate to a gap 46, resulting in loss of the charge at a single anode electrode 44.

Thus, when charge is split between two or more anode electrodes, the ideal case is that all of the charge will be collected at the anode electrodes 44. However, it is possible that some charge is lost between the anode electrodes 44. It is also possible that in such events, charge sensed at an anode electrode 44 falls below a certain threshold and may not register or be otherwise detected at that anode electrode 44, resulting in a loss of signal for that conversion event 48. In extreme examples, the resulting split charge may be insufficient (i.e., below the read-out threshold) at each anode electrode 44 to be read-out, resulting in no charge being detected at the anode electrodes 44 for a given conversion event 48.

Figure 3:
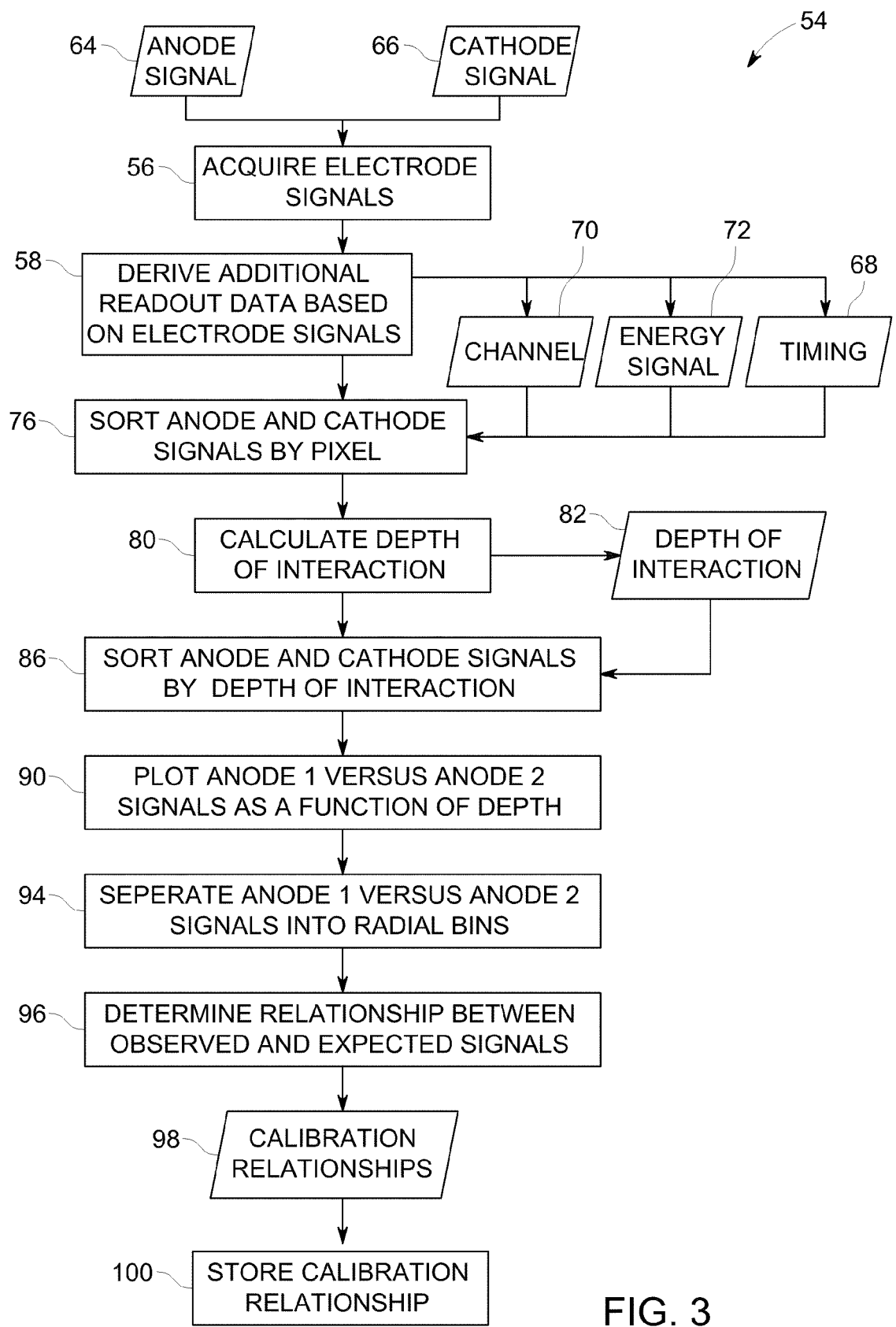
FIG. 3 is a flowchart depicting steps of an algorithm for addressing charge loss within a detector module in accordance with aspects of the present disclosure.

With the foregoing in mind, and turning to FIG. 3, one example of a method 54 for correcting for such charge losses is described. In particular, FIG. 3 describes steps of an algorithm for performing a calibration to address charge loss. In this example, subsets of the anode signals are made based on the relative position (e.g., depth and lateral position) of the anode signals in the detector. Appropriate corrections are then determined based on the observed signals and the expected signals and on the relative position associated with the signals.

In one implementation, the various described steps are performed for each combination of pixels (e.g., adjacent anode electrodes 44) at each depth of interaction within the conversion material 40 and for different lateral or angular positions relative to the pixels in question. For example, in one implementation lateral and/or angular position may be represented by respective "radial bins" that are derived based on plot of the relative frequency of observed events with a particular value of a first pixel ($P_1$) and a second pixel ($P_2$) such that the "radial" aspect corresponds to considering events which lie in the vicinity of a line through the origin that describes a constant ratio of $P_1$ and $P_2$. Thus, different radial bins may correspond to different ranges of the ratio of $P_1/P_2$.

In this example, data in the form of anode signals 64 (i.e., the charge read-out from one or more anode electrodes 44) and cathode signals 66 (i.e., the charge read-out from a cathode electrode 42) is acquired (block 56) during an examination or calibration session. Such read-out data may in turn be used to derive (block 58) additional data of interest, such as timing data 68 (e.g., the respective timings when charges are manifested at the respective anode electrodes 44 and cathode electrode 42), the anode, i.e., pixel, channel(s) 70 where charges are measured, and/or the energy signal 72 describing what is detected of the known gamma ray energy signal. In accordance with the depicted implementation, once suitable data is acquired, the anode signals 64 and cathode signals 66 are sorted (block 76) by pixel. In circumstances where a conversion event results in signal at two or more anode electrodes 44 (i.e., a charge sharing event) being detected, sorting may be done based on the anode electrode 44 that received the most charge or based on other suitable designation schemes.

Figure 4:
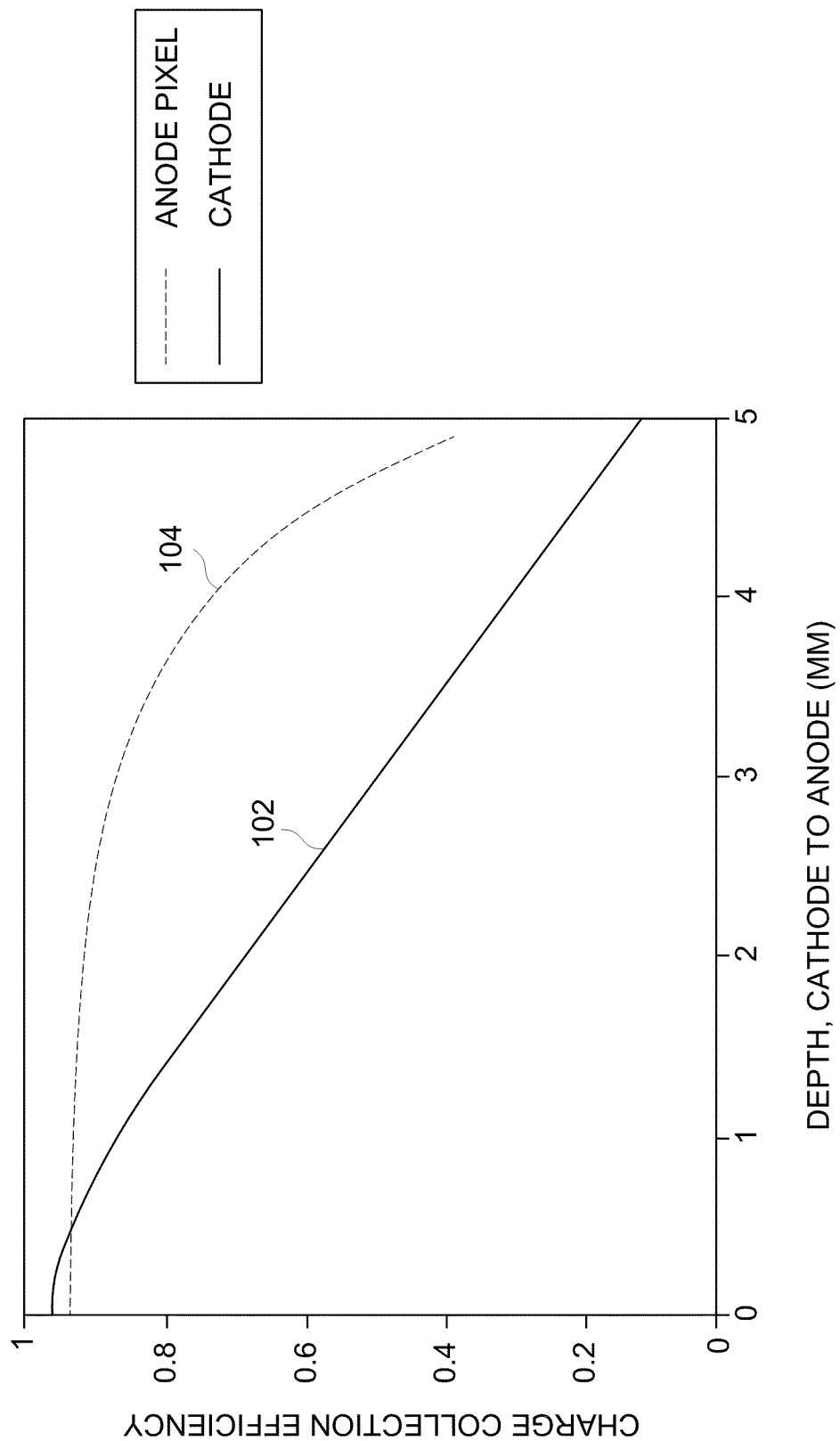
FIG. 4 is a graph depicting charge collection efficiency of an anode and cathode separately as a function of depth of interaction in accordance with aspects of the present disclosure.

A depth of interaction 82 is calculated (block 80) for each conversion event 48 using the ratio of the respective cathode signal 66 to anode signal or sum of anode signals 64 and/or using timing data 68. The anode signals 64 and cathode signals 66 may then be sorted (block 86) by the respective depths of interaction 82. By way of example and turning to FIGS. 4 and 5, curves 102, 104 of FIG. 4 show the relationship between depth of interaction and the amount of charge collected at the anode and cathode respectively. In this example, the charge collection efficiency describes the fraction of charge collected at the anode electrode(s) 44 and cathode electrode 42 for different depths of interaction. Noticeably, the cathode charge collection efficiency has a strong and almost linear dependence on the depth of interaction, and therefore may be used to determine the depth of interaction. Events occurring near the cathode will result in a more complete cathode signal, and events occurring deeper in the crystal will result in an incomplete cathode signal. In extreme cases, for conversion events 48 occurring near the anode, the cathode charge collection efficiency may be very poor such that a cathode signal is not detected. For instance, if the threshold for detection of a cathode signal is 40 keV, an interaction in which the deposited energy is 140 keV but where the charge collection efficiency is less than 0.28 may not be detected. For the most common interaction depths, closer to the cathode surface, the anode signal is less dependent on the depth of interaction.

Figure 5:
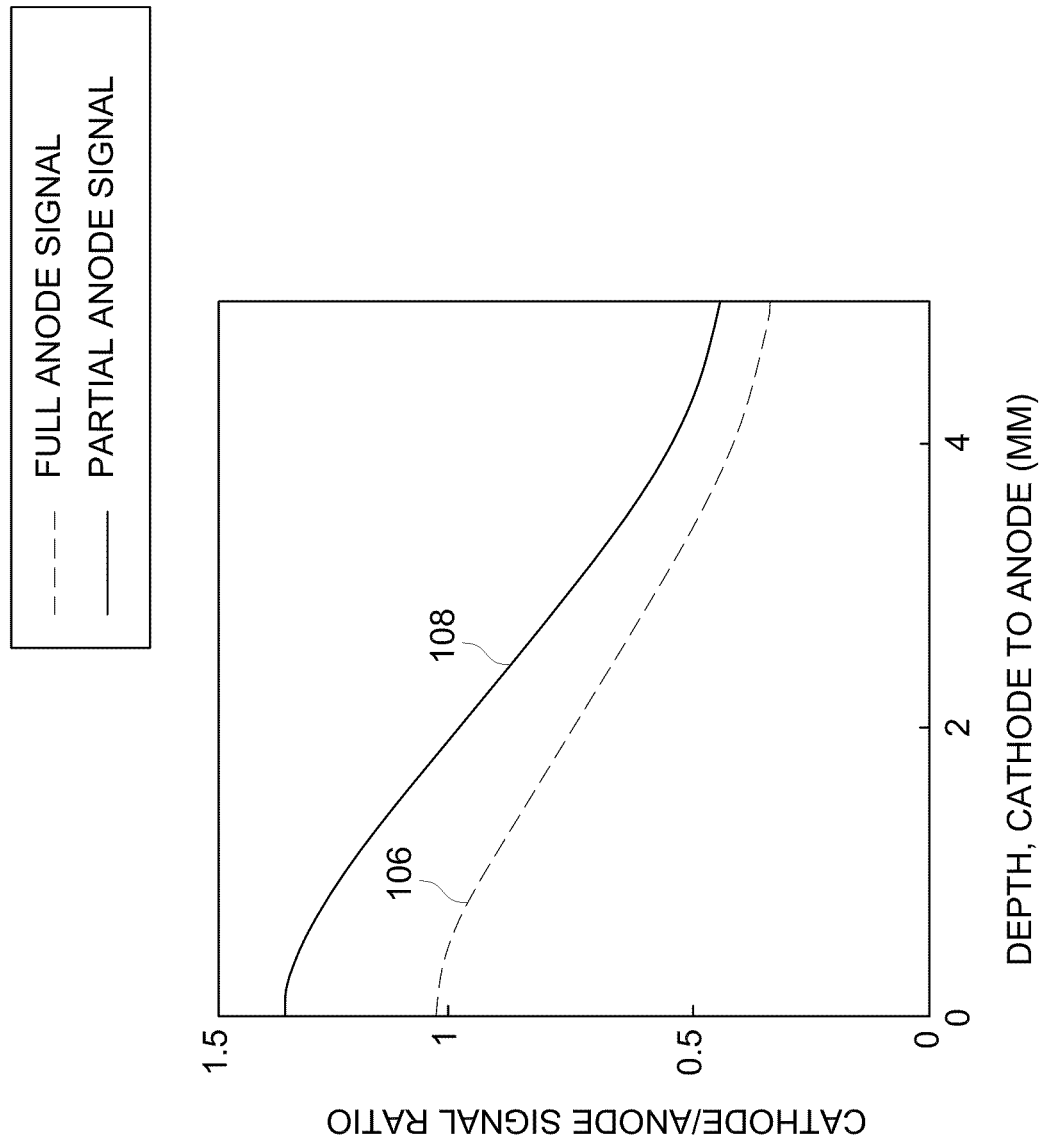
FIG. 5 is a graph depicting the cathode to anode signal ratio as a function of depth of interaction in accordance with aspects of the present disclosure.

Dividing the cathode charge collection efficiency by the anode charge collection efficiency, as depicted if FIG. 5, shows the relationship as a function of depth. For circumstances where the expected amount of charge is collected at the anode and cathode, the trend is depicted by line 106. However, if some charge is missing or not collected at the anodes, the trend shifts higher, as depicted by line 108. For the region of the curve represented by line 108, if not all the cathode signal and the anode signal is collected (i.e., if loss occurs with respect to both the cathode signal and anode signal), it may be difficult or impossible to distinguish this situation from the circumstance where the expected amount of charge for both the anode electrode and cathode electrode is detected. That is, the ratio may be similar or the same even though charge was lost at both the cathode and electrode. Thus, in certain circumstances, the ratio of the cathode signal to anode signal may be used to determine the depth of interaction 82 of a conversion event 48.

With the relationship depicted in FIG. 5 in mind, it may be appreciated that a larger ratio of cathode signal/anode signal may be indicative of a depth of interaction 82 closer to the cathode electrode 42. Likewise, a smaller cathode signal/anode signal ratio may be indicative of a depth of interaction 82 closer to the anode electrode 44. As discussed above, this may be true because a relatively small cathode signal 66 is detected, which may be indicative of holes 52 that are traveling slowly (relative to electrons 50) or which have failed to reach the cathode electrode 42 within the signal integration time.

In certain circumstances when the cathode signal/anode signal ratio is greater than one, less anode signal was detected than what was expected (as indicated by the larger cathode signal relative to the anode signal). In a circumstance when only one anode electrode 44 is detected as having a charge and the cathode signal/anode signal ratio is greater than one, it is possible that signal should have been detected from a second anode electrode 44 as well but, due to charge loss and/or the failure of the charge at one of the anode electrodes 44 to exceed the threshold associated with read-out, the charge at one of the anode electrodes 44 is not detected. As noted above, the cathode/anode signal ratio curve, as represented by line 108, is shown in FIG. 5 for the charge loss case. Further, as noted above, in the case where the cathode signal is also less than the complete signal, the difference between the curves can not be readily distinguished. That is, it is not known whether there was also an incomplete signal at the anode electrode as well as at the cathode electrode. Further, if charge is measured at two different anode electrodes 44 as well as at the cathode electrode 42, these three signals may be used to triangulate the position (i.e., the depth of interaction 82 and lateral position) of the conversion event 48. Conversely, as discussed above, if no cathode signal is detected but two anode signals are detected, the conversion event 48 likely occurred near the anode electrodes 44. Such information may be used to select a suitable a charge loss calibration curve or factor using three signal triangulation data, as discussed herein.

With the foregoing discussion of depth of interaction 82 in mind and returning to FIG. 3, in an implementation, where more than one anode signal 64 is present, the respective signal of the first anode may be plotted (block 90) against the respective signal of the second anode as a function of the calculated depth of interaction 82. The respective first anode versus second anode signals may then be sorted (block 94) into radial bins representing the respective lateral position of the charge in relation to the first and second anodes where charge sharing was detected. A calibration relationship 98 (e.g., a calibration factor, offset, or curve) may be determined (block 96) between the expected signals and the observed signals for the respective depth of interaction and radial location. For example, the calibration relationship may describe a difference calculated between expected and observed signals (e.g., anode signals) or mean, median, or modes derived from such observed and expected signals. Likewise, the calibration relationship may be based on the offset or shift that would align a peak fitted to a spectrum (i.e., an observed spectrum) with one or more characteristic energy peaks (i.e., an expected spectrum) or based on the ratio of mean peak height in the observed spectrum. In a further embodiment, the calibration relationship may be based on or describe the multiplication factor that provides the best fit between the expected and observed energy spectra. The calibration relationship, once determined, may then be stored (block 100) for subsequent use during examinations or other imaging sessions.

Figure 6:
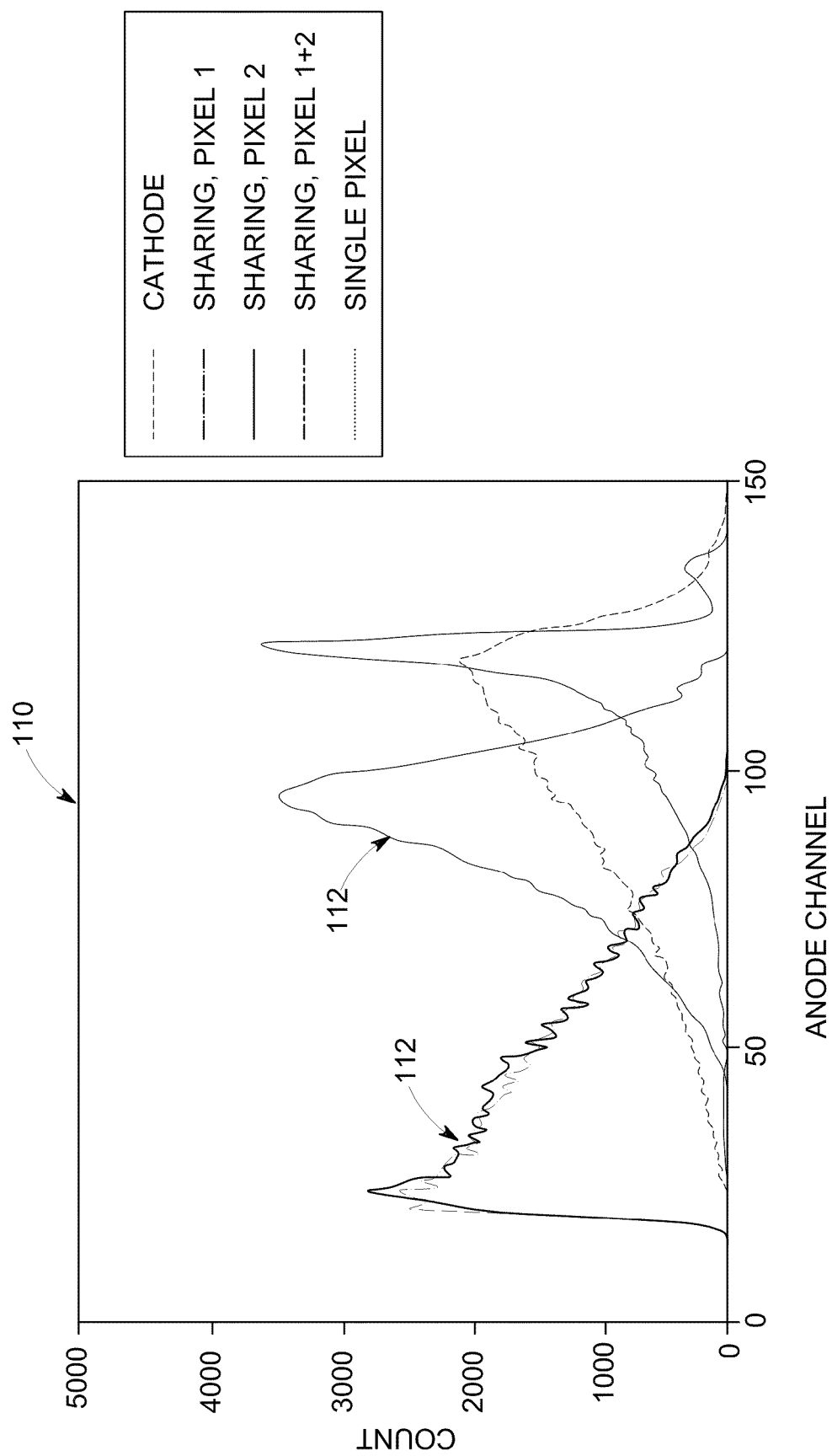
FIG. 6 depicts a plot of histograms for a single pixel, in accordance with aspects of the present disclosure.
Figure 7:
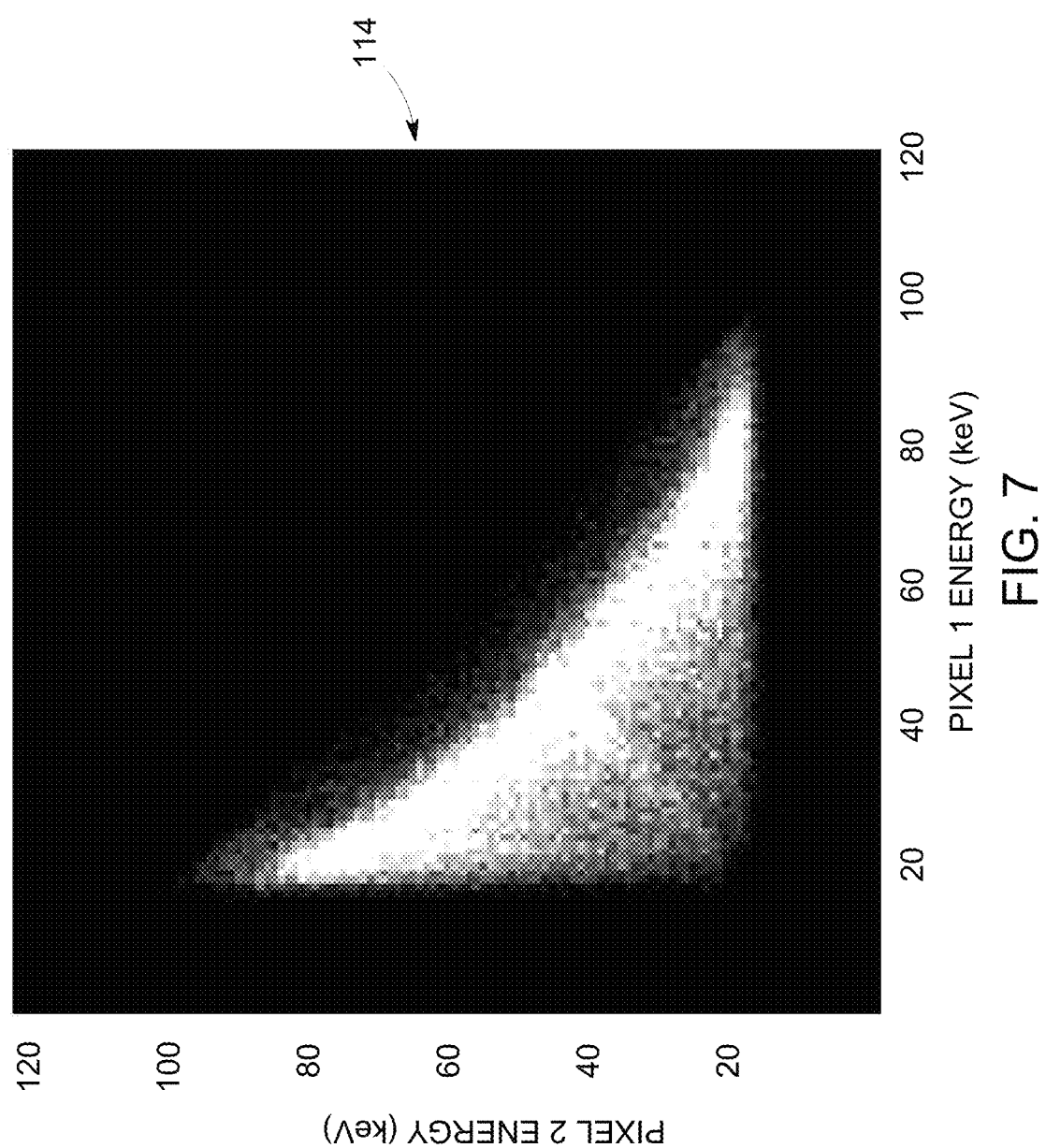
FIG. 7 depicts a plot of charge sharing events as first anode signals versus second anode signals in accordance with aspects of the present disclosure.

Turning to FIGS. 6-13, an example of the preceding algorithm is described for correcting the signal measured at two anode electrodes for a single depth of interaction and a single radial bin (i.e., for a single conversion event 48). Turning to FIG. 6, in this example a series of histograms 110 depicts the various acquired signals at one pixel. As will be appreciated, the various histograms 110 (such as the single pixel histogram) are provided for illustration and are not necessarily depicted to scale. In the depicted example, histograms 112 represent charge sharing events between the pixel of interest $P_1$ and one or more neighboring pixels $P_2$. Based on these acquired signals, and turning to FIG. 7, for conversion events 48 where it is determined that charge sharing has occurred between anode electrodes 44, a plot 114 may be generated depicting the signals acquired by a first pixel against the signals acquired by the one or more second pixels for all interaction depths. One or both of these steps may generally correspond to steps performed as part of acquiring calibration data as depicted at block 62 of FIG. 3.

Figure 8:
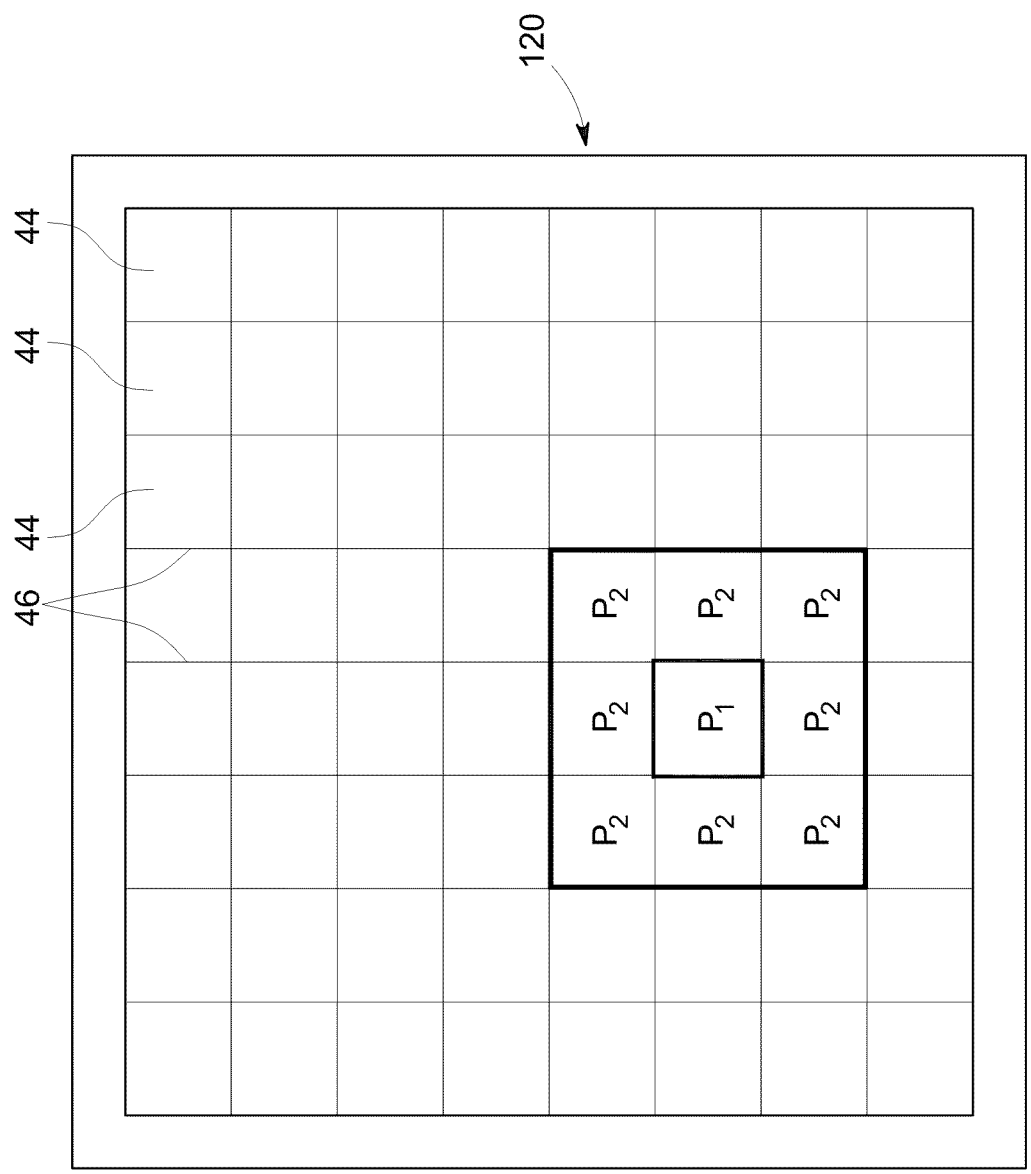
FIG. 8 depicts a plan view of a pixel grid in which a pixel of interest and neighboring pixels are emphasized.

Next, signals may be sorted based on the respective anode pixel for charge sharing events, as described at block 76 of FIG. 3. By way of example, FIG. 8 depicts an example of an anode pixel grid 120 in which one anode electrode (e.g., pixel $P_1$) is depicted with neighboring anode electrodes (e.g., pixels $P_2$). As will be appreciated, charge sharing may occur between pixel $P_1$ and one or more of neighboring pixels $P_2$. As discussed herein, calibration may occur for each pixel pair separately or for pixel $P_1$ and all neighboring pixels $P_2$ jointly.

Figure 9:
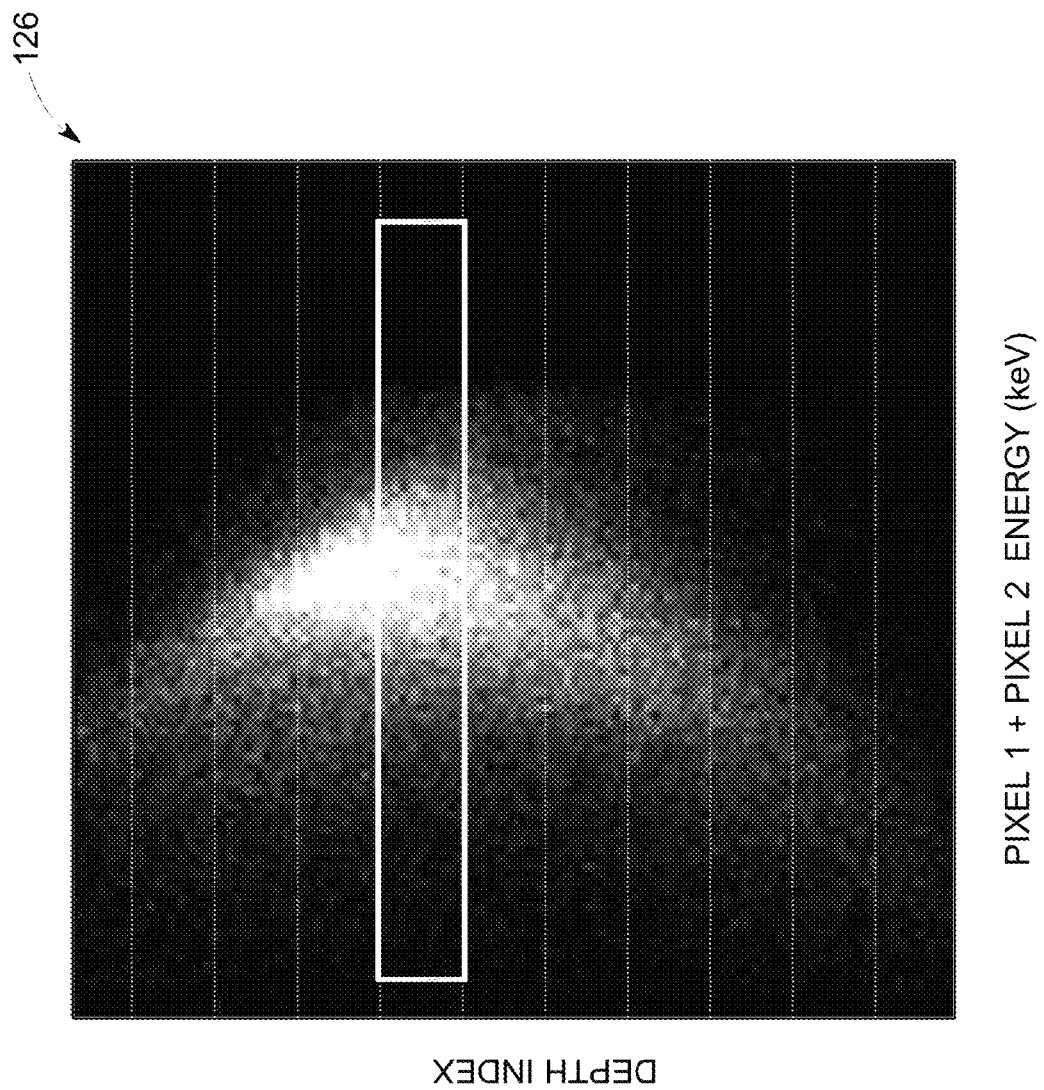
FIG. 9 depicts a plot of cathode/anode signal ratio versus anode signals indicating the of depth of interaction, in accordance with aspects of the present disclosure.
Figure 10:
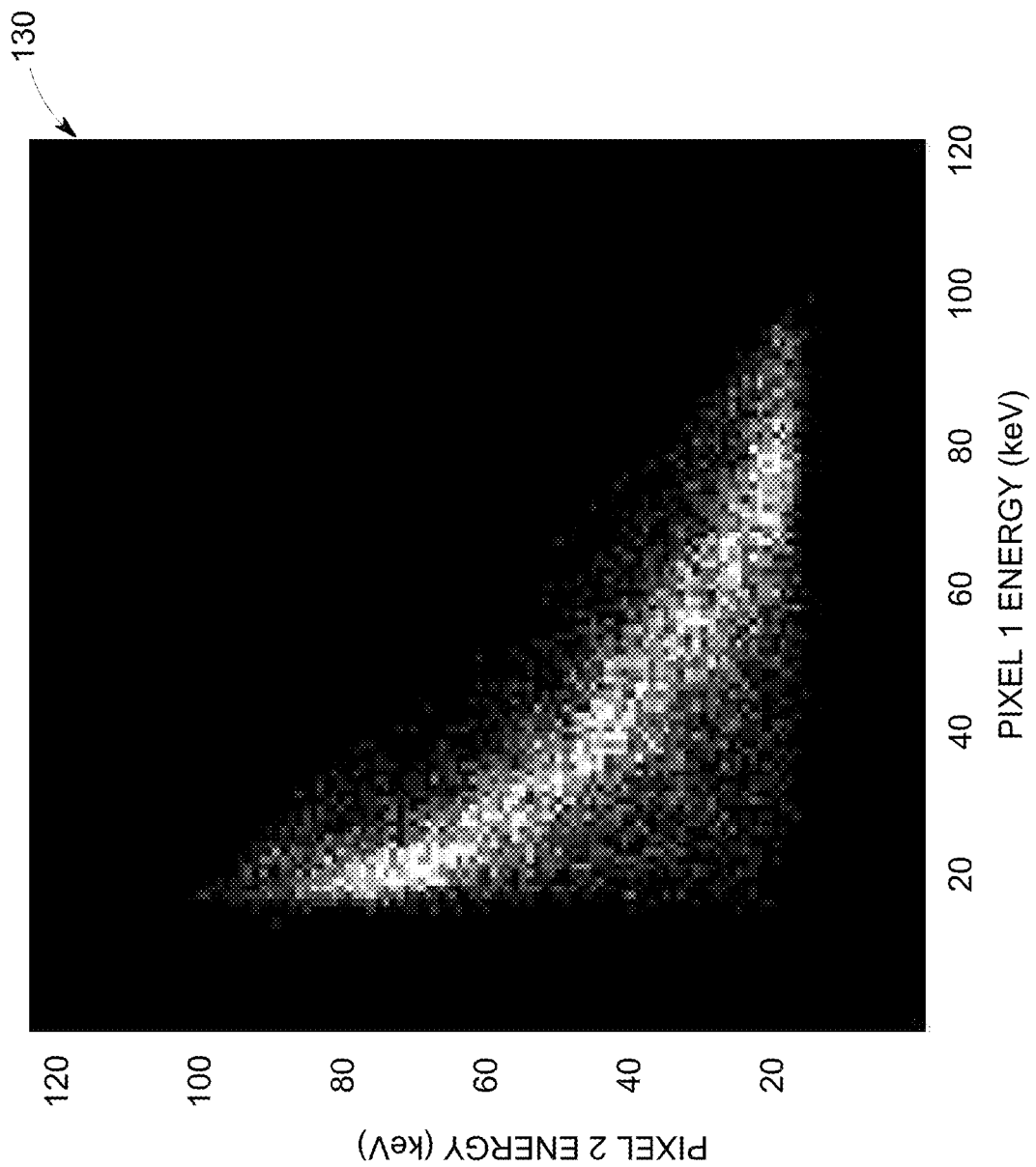
FIG. 10 depicts a plot of first anode signals versus second anode signals at a specified depth of interaction in accordance with aspects of the present disclosure.
Figure 11:
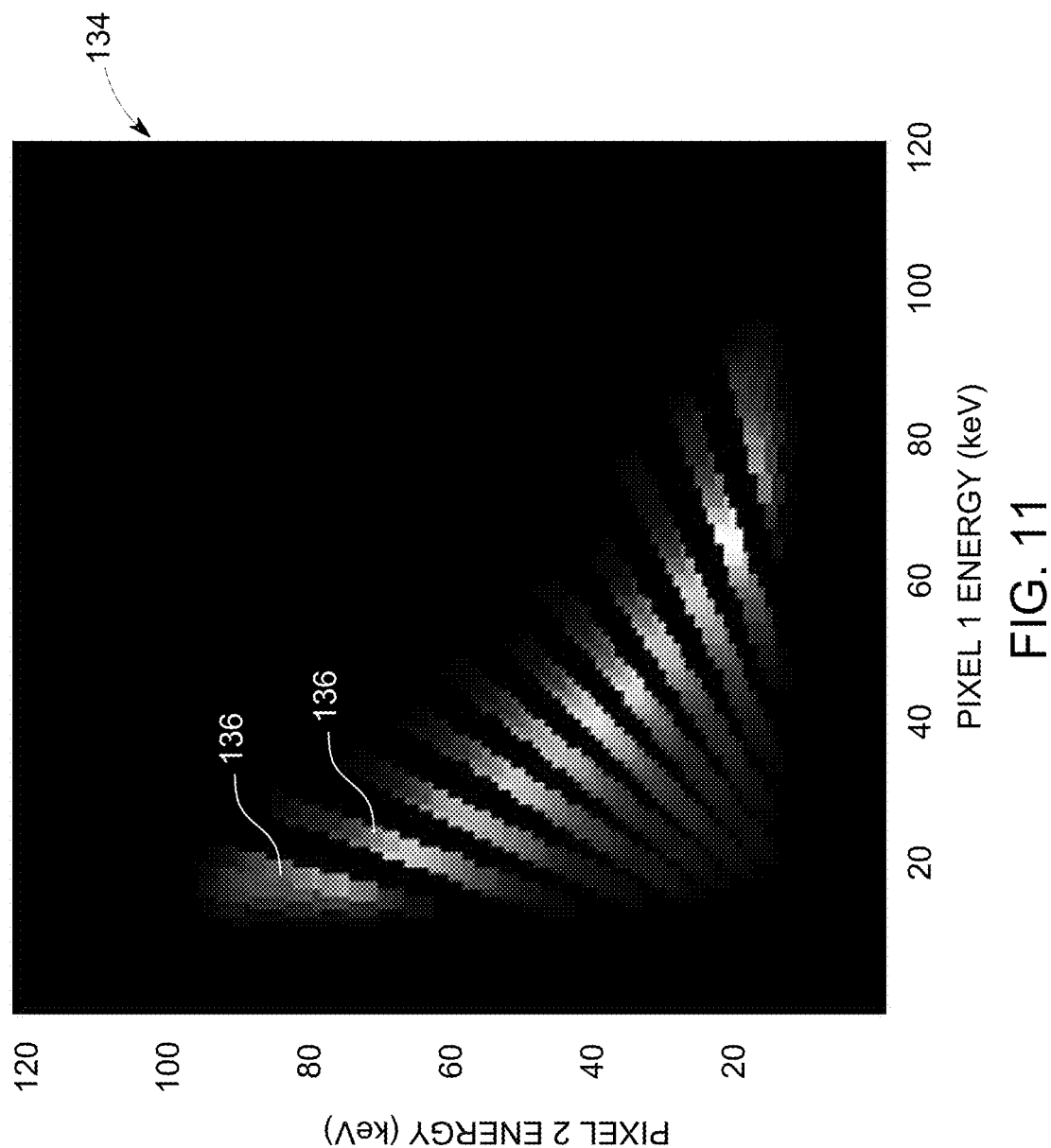
FIG. 11 depicts a plot of first anode signals versus second anode signals with a sampling of radial locations in accordance with aspects of the present disclosure.
Figure 12:
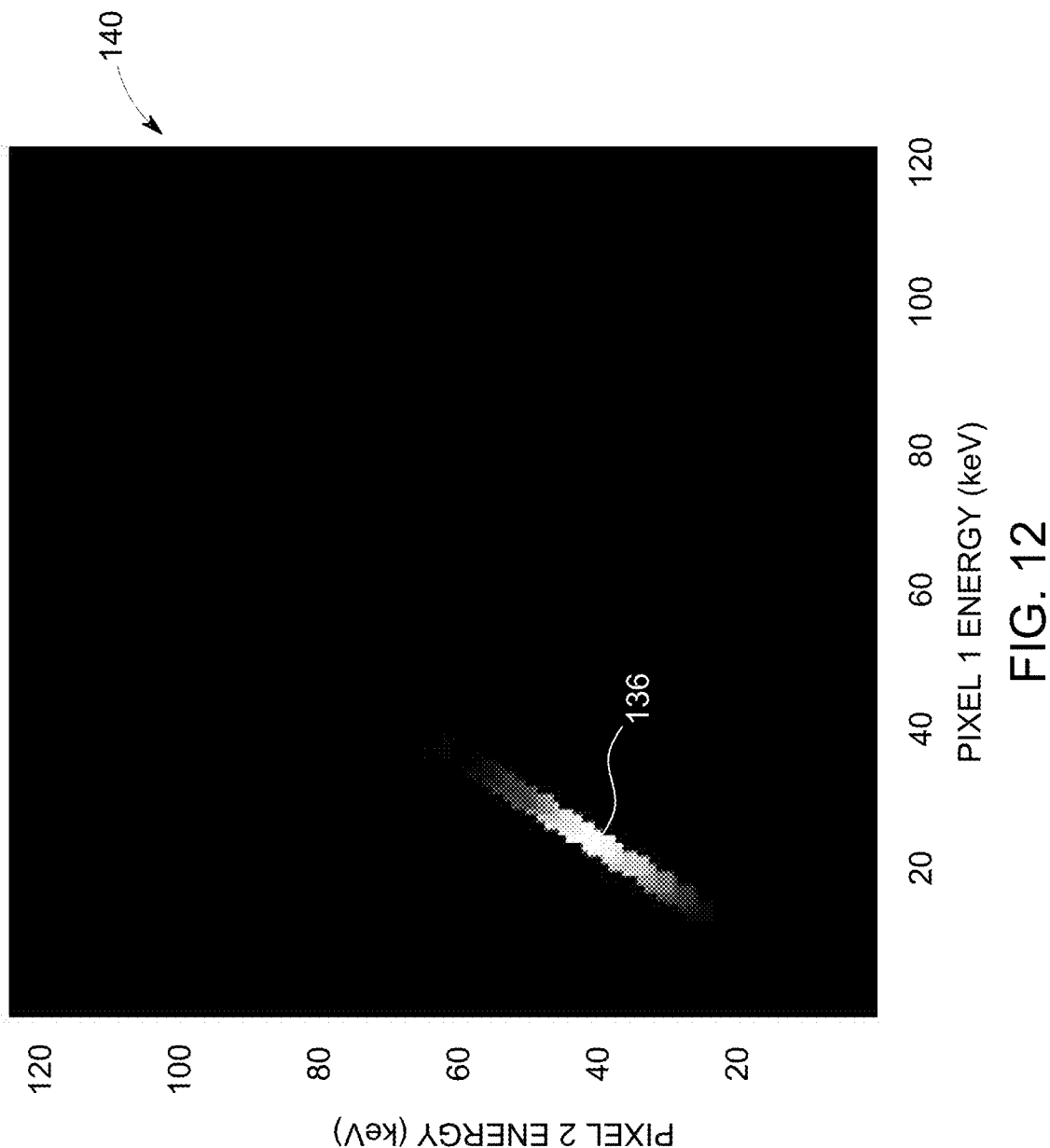
FIG. 12 depicts a plot of first anode signals versus second anode signals at a specified radial location in accordance with aspects of the present disclosure.

Turning to FIG. 9, the depth of interaction 82 (as determined by the cathode/anode signal ratio) may be plotted versus the anode signal 64 for the pixel of interest, as depicted in illustration 126. Alternatively, instead of using the cathode/anode signal ratio to sort anode signals 64 by depth of interaction 82, rise time at the electrodes may instead be used to provide information about the depth of interaction 82. In such an embodiment, rise-time may be plotted as the y-axis.

In this manner, the respective anode signals 64 may be sorted or binned in accordance with the depth of interaction 82 of the associated conversion event 48 giving rise to the respective anode signals 64. Based on these depth of interaction determinations, the signals for a first anode electrode may be plotted against the signals for a second anode electrode at a given depth of interaction, as depicted in the plot 130 of FIG. 10. The presence of two anode signals indicates likely charge sharing events and the various anode signals for such charge sharing events are sorted by depth of interaction 82 such that the signals associated with each depth of interaction may be processed separately.

While the preceding describes the process of determining the depth of interaction and sorting in accordance with the depth of interaction, lateral position of the event with respect to pixel geometry may also be taken into account in certain embodiments. For example, turning to FIG. 11, a plot 134 is depicted in which the first anode versus second anode signals are sorted into radial bins 136, where each radial bin 136 corresponds to a different radial or angular position or segment relative to the first anode electrode 44, i.e., pixel $P_1$. Any number of radial bins may be employed (e.g., 3, 4, 6, 8, 10, 12, and so forth) In FIG. 12, the plot 140 of the first anode versus second anode signals for a single radial bin 136 are sorted out for further processing. Thus, in this manner signals corresponding to a single depth of interaction and a single radial bin for the anode electrode corresponding to pixel $P_1$ and its neighboring pixels $P_2$ are determined.

Figure 13:
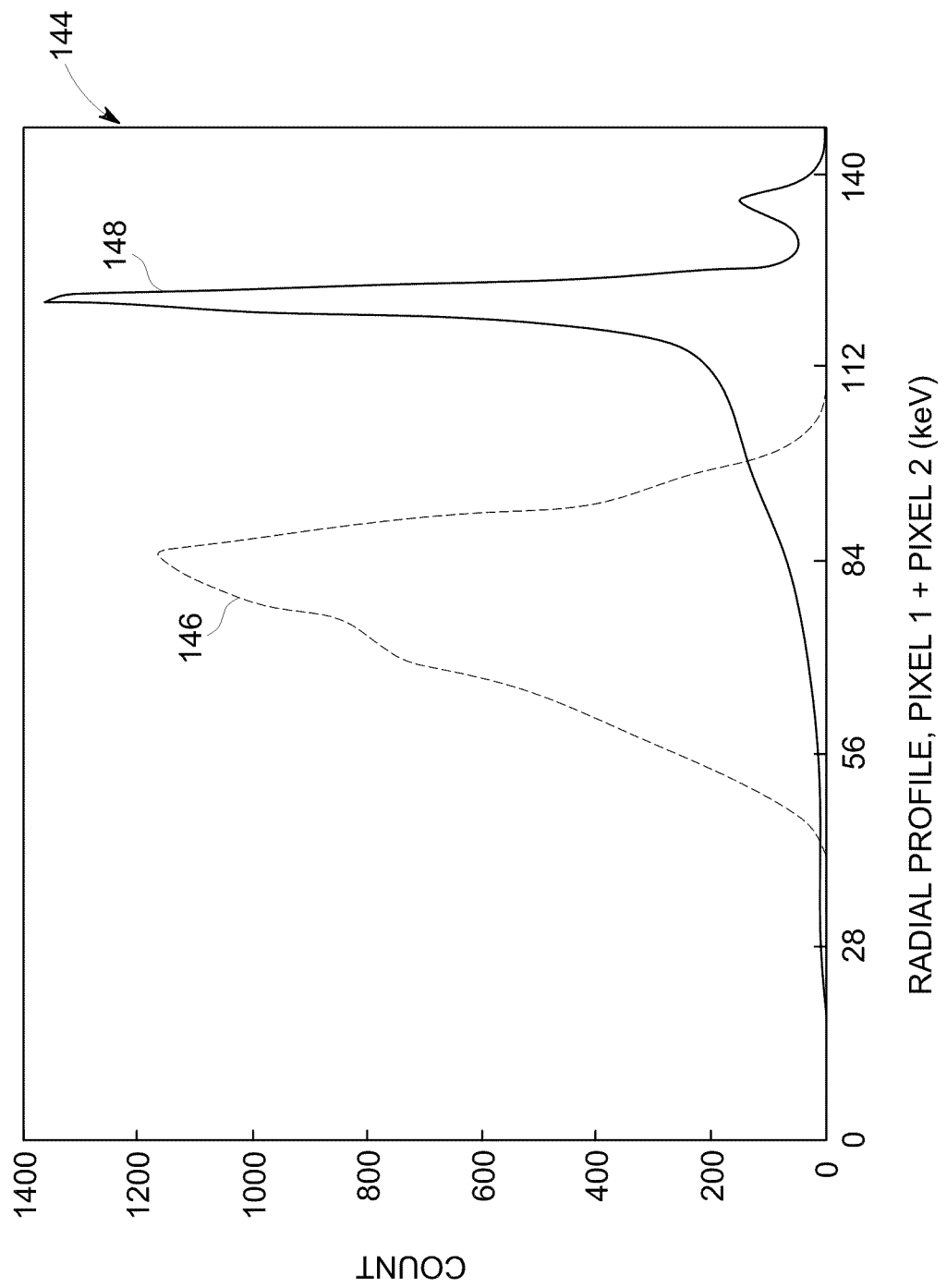
FIG. 13 depicts a plot of observed count distribution and expected count distribution along a radial bin at a specified depth of interaction in accordance with aspects of the present disclosure.

At this point, the selected radial sample may be used to find charge loss correlation for the selected depth of interaction bin. For example, profiles 144 of observed counts 146 along the selected radial bin versus total energy may be plotted and compared to the expected counts 148. As depicted in the plot of FIG. 13, the differences between the observed counts 146 and the expected counts 148 is indicative of charge loss. Based on this comparison, a correction value or factor may be determined for pixel $P_1$ and the one or more respective pixels $P_2$ for the selected depth of interaction 82 and radial bin 136. For example, in one embodiment the appropriate correction may simply be to determine the necessary offset value needed to align the mean, mode, and/or medians of the respective count distributions. That is, in such an implementation, the distribution of observed counts 146 is shifted to where it is expected. This correction value may then be stored and used in subsequent imaging operations.

While the preceding described one manner in which a charge loss correction may be calculated for a pixel for one depth of interaction and radial bin, in certain embodiments it may be desirable to determine charge sharing and loss calibration for all signal combinations. For example, such an approach may allow generation of a continuous curve describing charge loss behavior and the appropriate correction factors to be employed in processing acquired signal data. In such implementations, the detected events (i.e., radiation conversion events) may be sorted or categorized by their respective depths of interaction and lateral positions (e.g., location, orientation, and so forth) within the radiation detector. Count profiles may be generated for the frequency of occurrence of sums of a set of anode signals associated with the detected events. A fraction of signal lost may then be determined for particular values of depth of interaction and/or lateral position.

Figure 14:
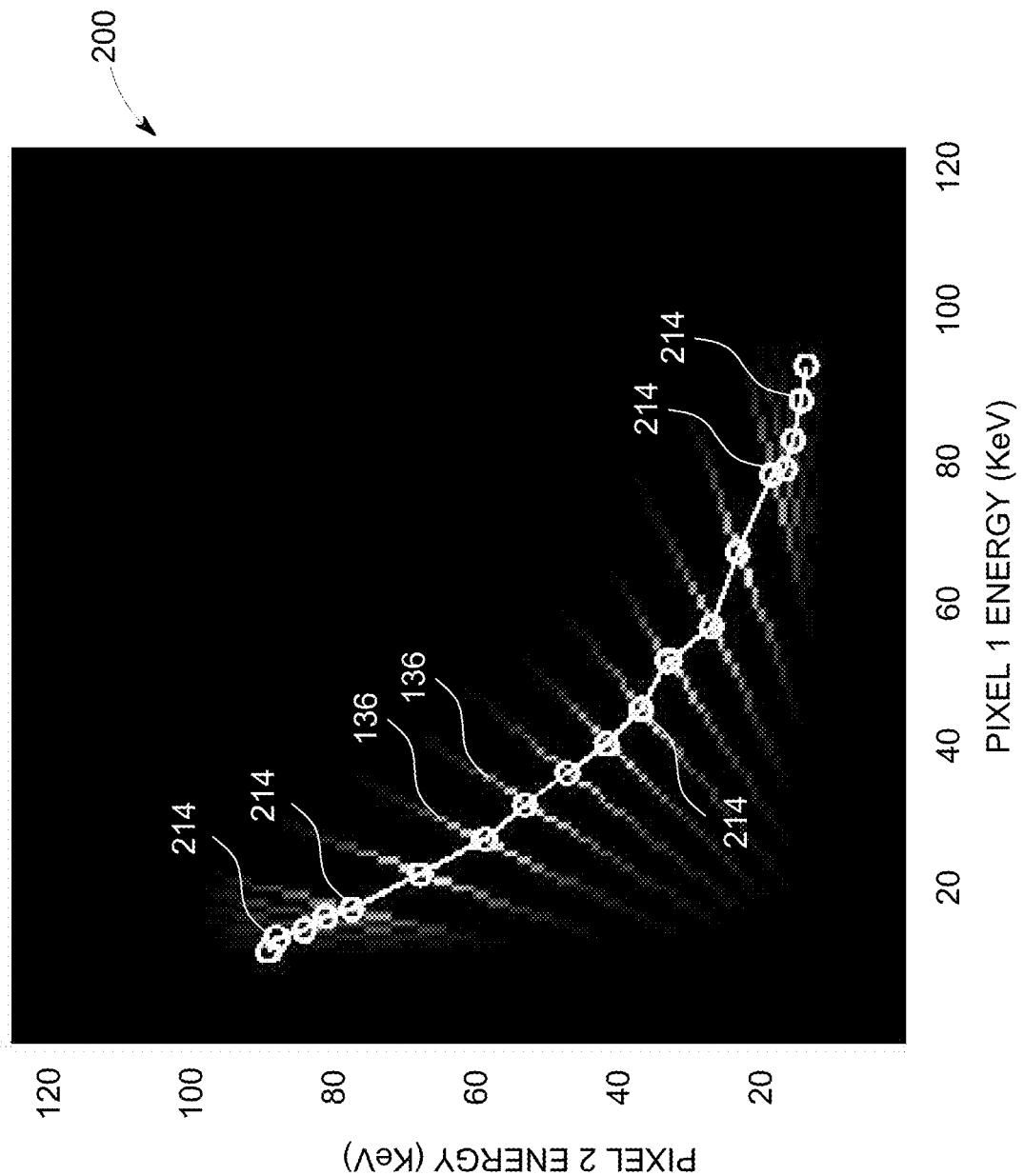
FIG. 14 depicts a plot of first anode signals versus second anode signals at a specified depth of interaction in accordance with aspects of the present disclosure.
Figure 15:
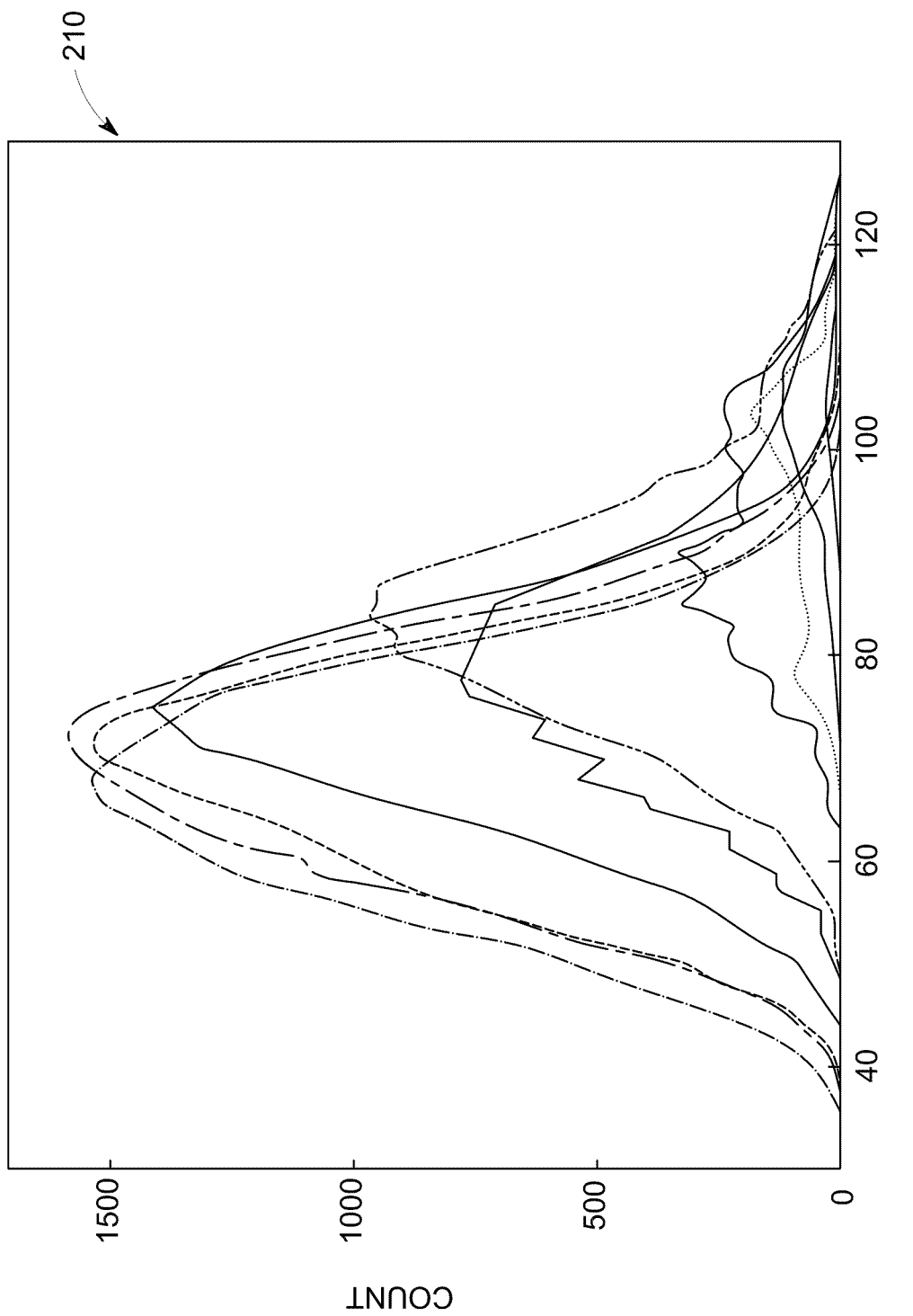
FIG. 15 depicts a count profile along radial lines in accordance with aspects of the present disclosure.
Figure 16:
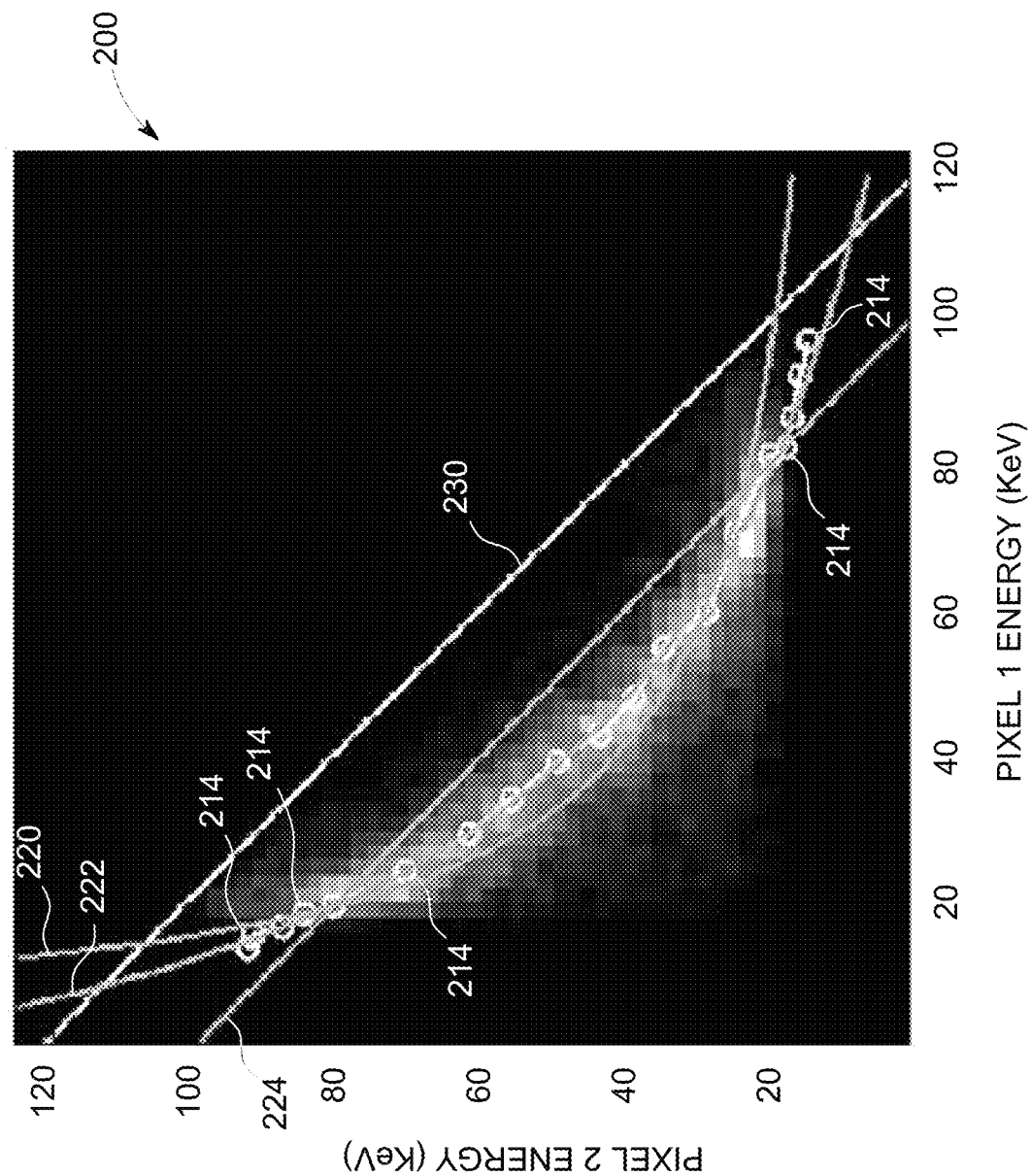
FIG. 16 depicts the fitting of curves to data points sampled from each radial sample in accordance with aspects of the present disclosure.

Turning now to FIGS. 14-21, an example of one such approach for correcting for charge loss for combinations of signals is described. Turning to FIG. 14, an initial plot 200 is depicted in which energy at a first anode electrode (i.e., $P_1$) is plotted against one or more second anode electrodes (i.e., $P_2$) at a specified depth of interaction 82. In addition, count profiles 210 are generated from the data along radial lines, as depicted at FIG. 15. That is, a profile is generated for each radial bin 136 identified or specified for the data. The count profile 210 may in turn be used to identify representative points $(P_1, P_2)$ 214 of data for each radial bin 136.

Figure 17:
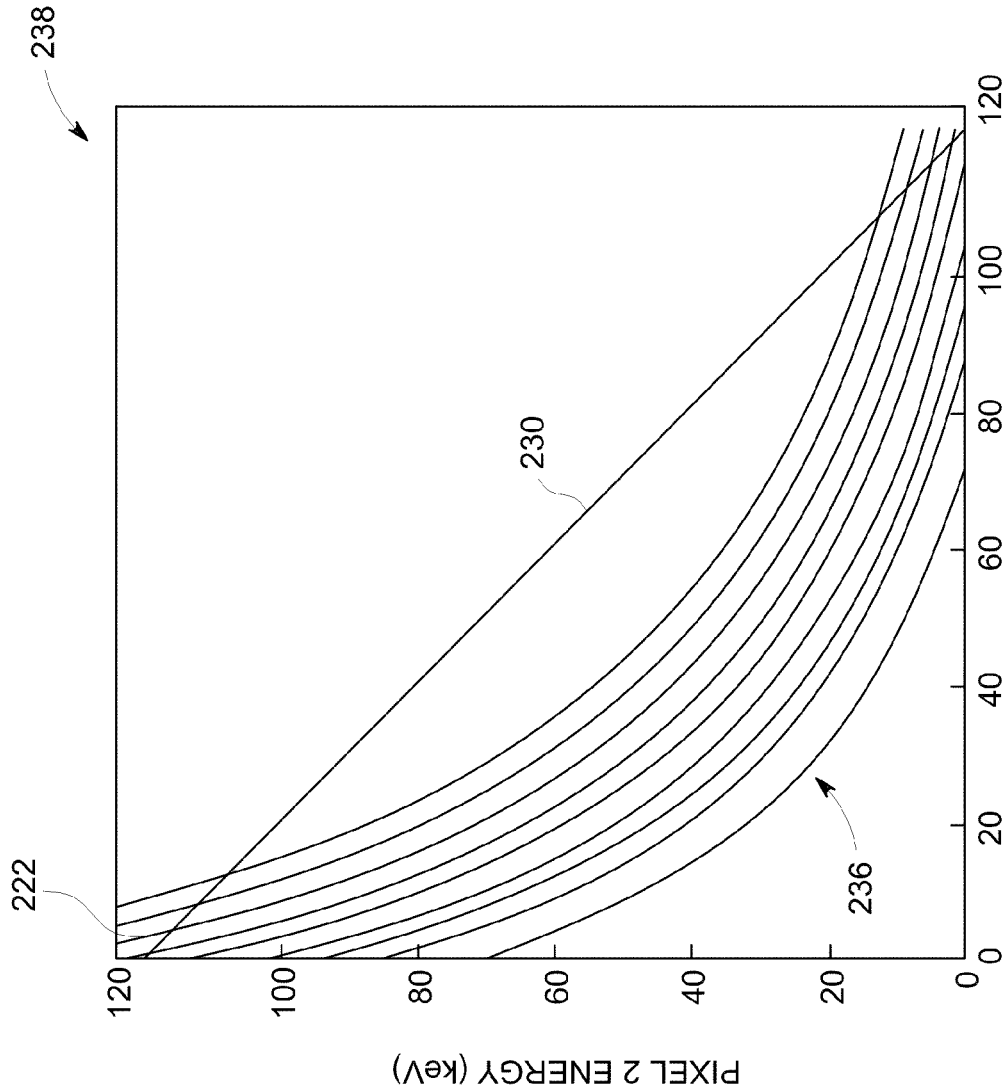
FIG. 17 depicts a plot of curves fit for different depths of interaction in accordance with aspects of the present disclosure.

As depicted in FIG. 17, in one embodiment, one or more curves may be fit to the data points 214. In the depicted example, three curves 220, 222, 224 are fit to the data points 214. In this example, the curve 222 with the least error, i.e., the best fit, (as determined by the difference between the curves 220, 222, 224 and the data points 214) is selected for subsequent processing. In FIG. 17, line 230 is also plotted which depicts the expected energy. The difference between the expected energy line 230 and the data points 214 (or the curve 222 fitted to the data points 214) represents the charge loss observed.

The curve 222, which provides the best fit, may be used as the basis for plotting corresponding trend lines 236 for different depths of interaction, as depicted in plot 238 of FIG. 17. As will be appreciated, the curve 222 could also be a piecewise combination, spline, or other known method. As depicted in plot 238, the trend lines 236 nearer the center of the plot 238 (i.e., nearer the expected energy line 230) generally correspond to depths of interaction nearer the cathode electrode 42 while the trend lines 236 nearer the exterior of the plot 238 (i.e., nearer the origin of the plot) generally correspond to depths of interaction nearer the anode electrodes 44. In this manner, descriptive curves for different depths of interaction may be derived using the known relationships between the expected charges associated with different depths of interaction.

Figure 18:
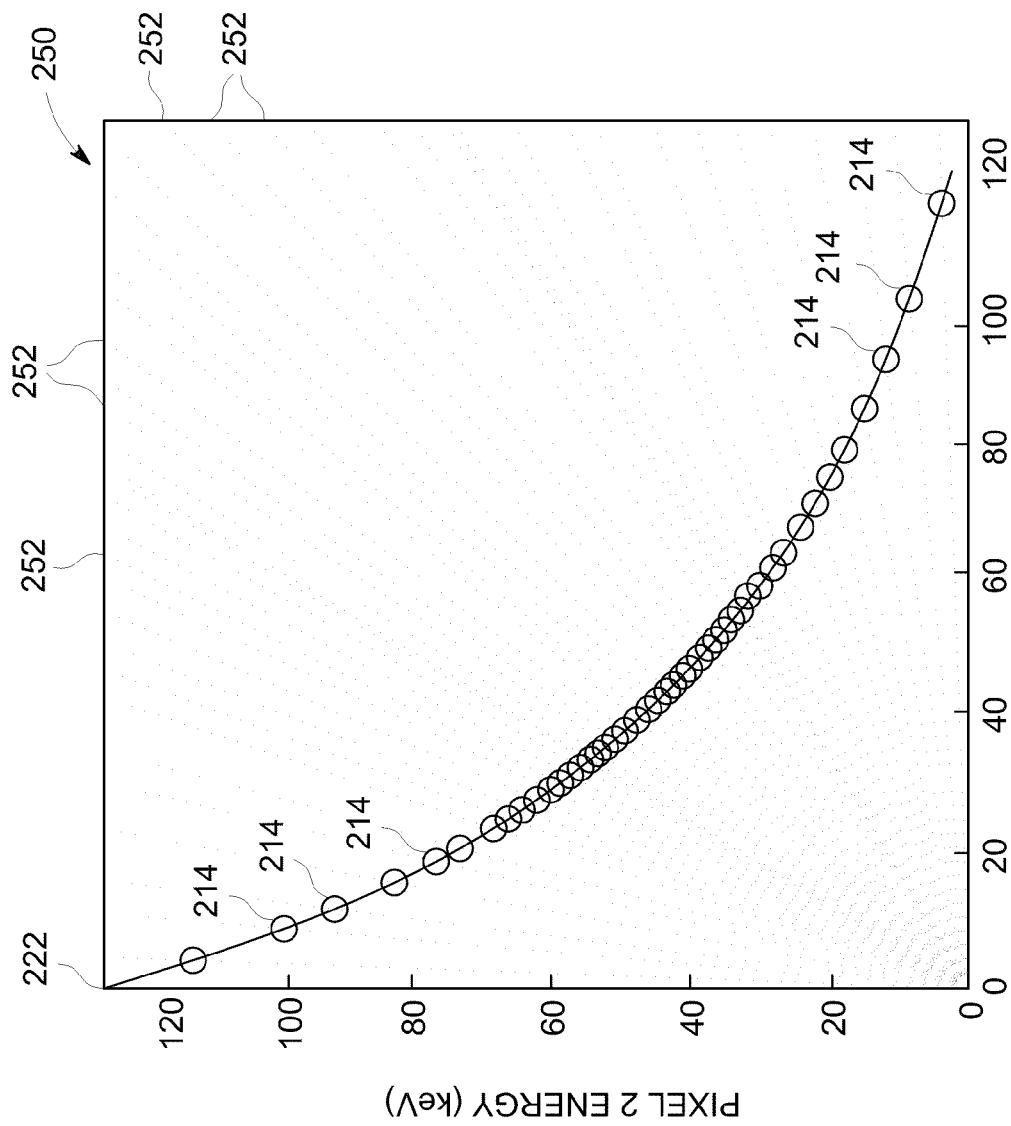
FIG. 18 depicts the intersection of radial lines with a curve fit to the sampled data points in accordance with aspects of the present disclosure.
Figure 19:
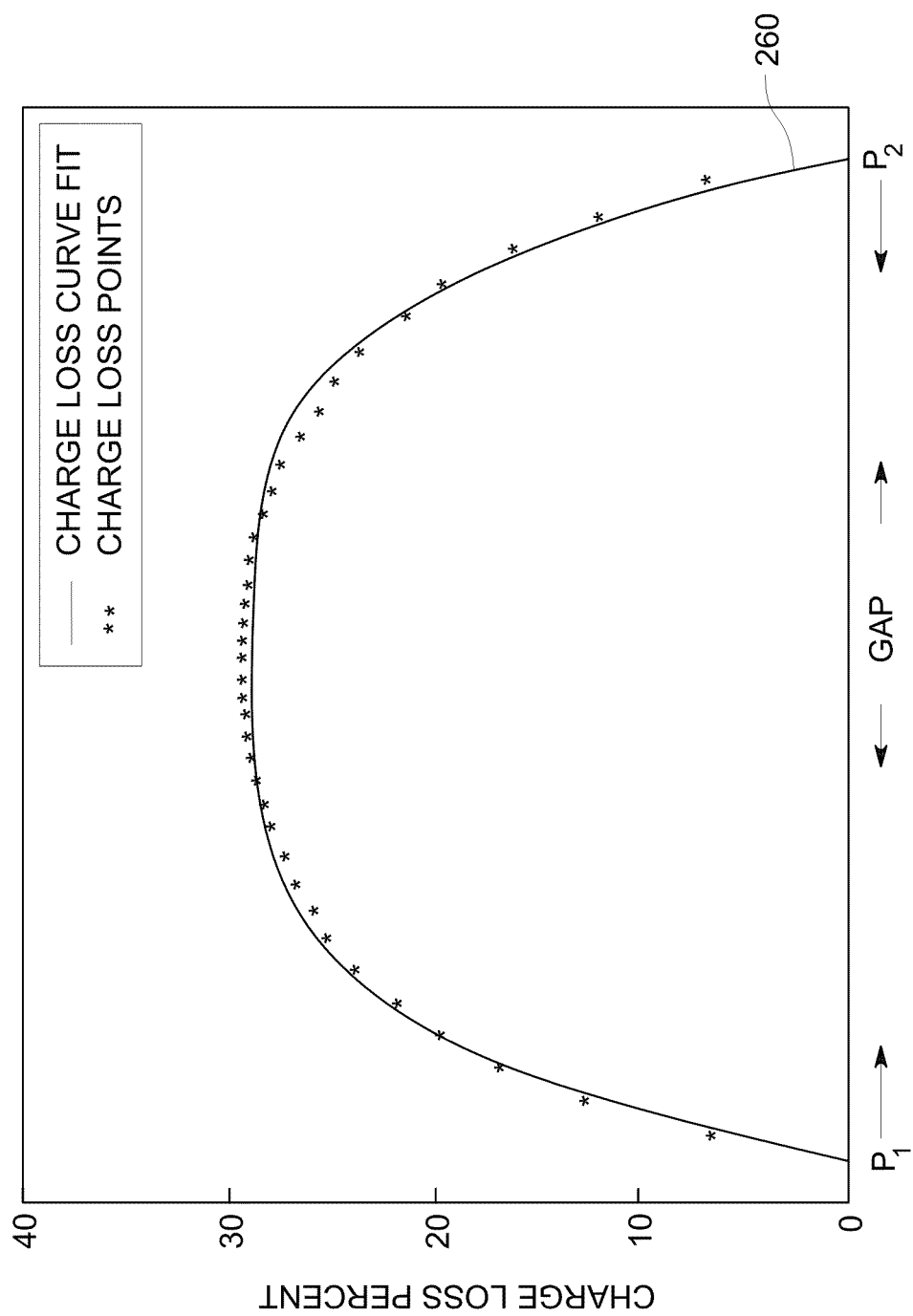
FIG. 19 depicts a charge loss curve in accordance with aspects of the present disclosure.

Similarly, turning to plot 250 of FIG. 18, the data points may also be radially sampled. For example, as depicted in plot 250, the intersection of radial lines 252 with the curve 222 that provides the best fit may be used rebind the sampled data points 214 as a function of angle where the angle represents the lateral positioning from the first anode pixel to the second anode pixel. For example, in the depicted plot 250, $P_1$ energy increases and $P_2$ energy decreases as the position of the interaction approaches $P_1$. Conversely, $P_2$ energy increases and $P_1$ energy decreases as the position of the interaction approaches $P_2$. For intermediate values of $P_1$ and $P_2$ energy, the position of the interaction is occurring near the gap 46 separating $P_1$ and $P_2$.

Once the radial and depth of interaction information is derived in this manner, differences between the radial samples from the expected energy may be determined. For example, turning to FIG. 19, a charge loss curve 260 is plotted based on the differences between the radial samples from the expected energy, as determined from the plots of FIGS. 17 and 18. Such a charge loss curve 260 may be plotted as a function of angle from the origin (0,0) to $(P_1, P_2)$ energies. That is, the charge loss curve 260 may be fit as a function of angle, thereby describing the amount or percent of charge lost as a function of angle, and the angle describes the charge loss for events occurring along different lateral positions with respect to anode electrodes 44.

Figure 20:
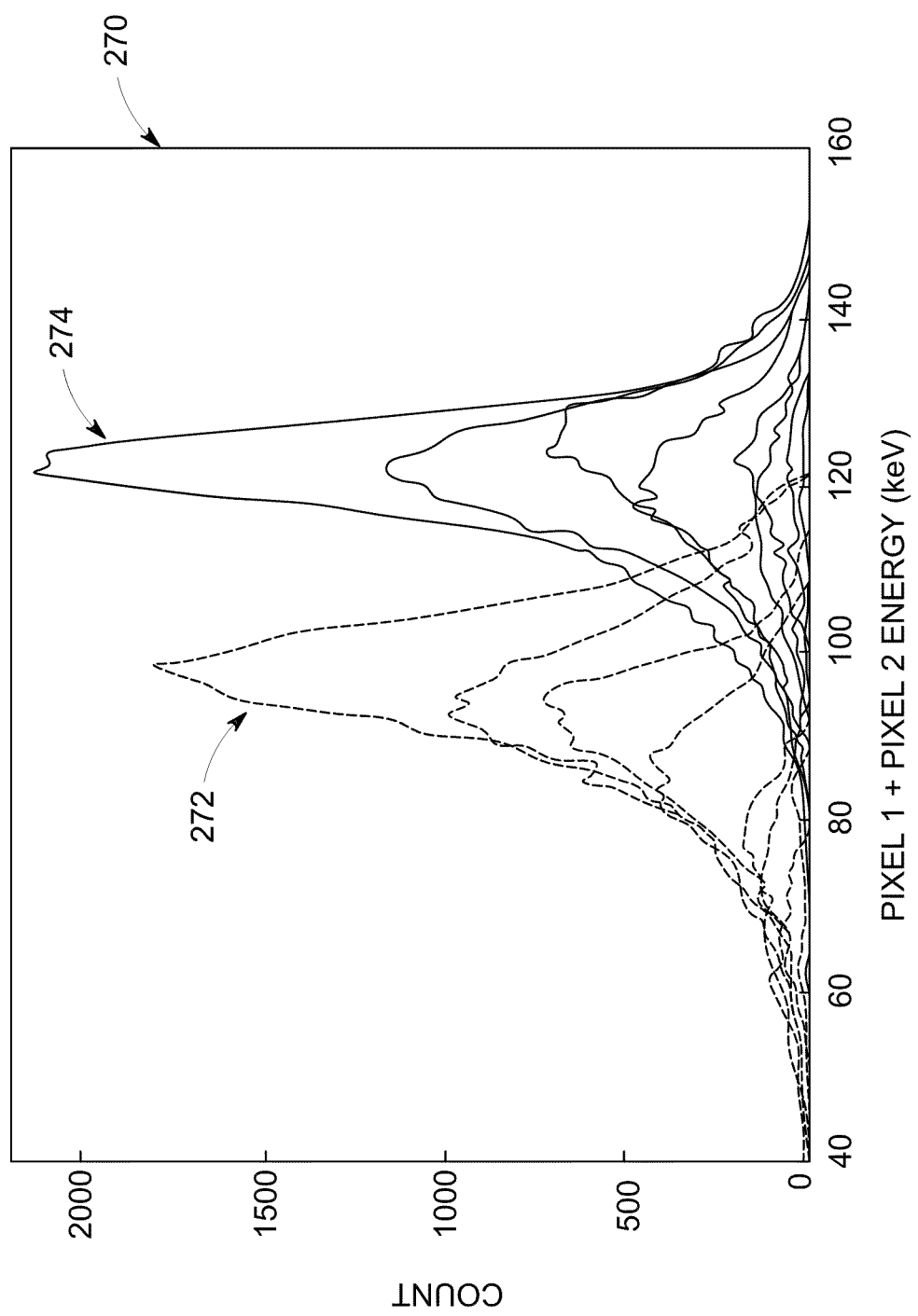
FIG. 20 depicts histograms of combined charge sharing anode signals before and after correction plotted for each depth of interaction in accordance with aspects of the present disclosure.

Next, the correction factor for each data point 214 may be determined, as depicted in plot 270 of FIG. 20. For example, using the plots of FIGS. 17 and 19, the charge loss curve 260 may be used to shift data points, as a function of angle, for each depth of interaction bin. As depicted in FIG. 20, acquired data in each depth of interaction bin is characterized by a separate distribution. Distributions 272, represented by dotted lines, are the energy histograms for combined anode energies at different depths of interaction prior to correction using the charge loss curve 260 while distributions 274, represented by solid lines, describe the energy histograms at different depths of interaction after correction using the charge loss curve 260.

Figure 21:
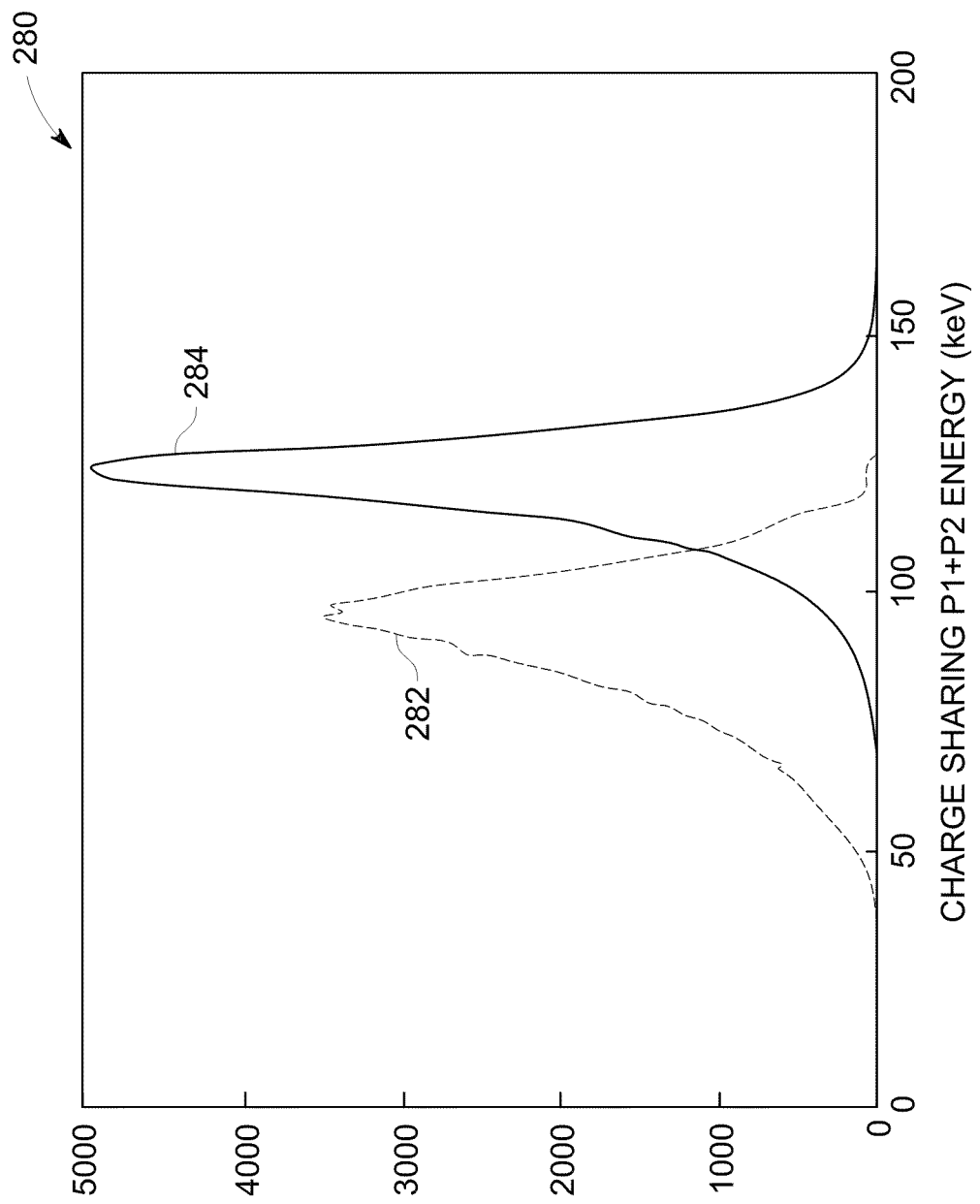
FIG. 21 depicts histograms of combined charge sharing anode signals before and after correction for all events and depths of interaction in accordance with aspects of the present disclosure.

The respective distributions for each of the depth of interaction bins may be combined, as depicted by plots 280 of FIG. 21, to provide a combined charge sharing spectrum. By way of example, spectrum 282, represented by a dotted line, describes the combined charge sharing spectrum prior to correction for charge losses. Spectrum 284, represented by a solid line, describes the charge sharing spectrum after correction for charge losses. The corrected charge sharing spectrum 284 may be stored and subsequently used for correcting for charge loss in subsequent imaging operations.

Figure 22:
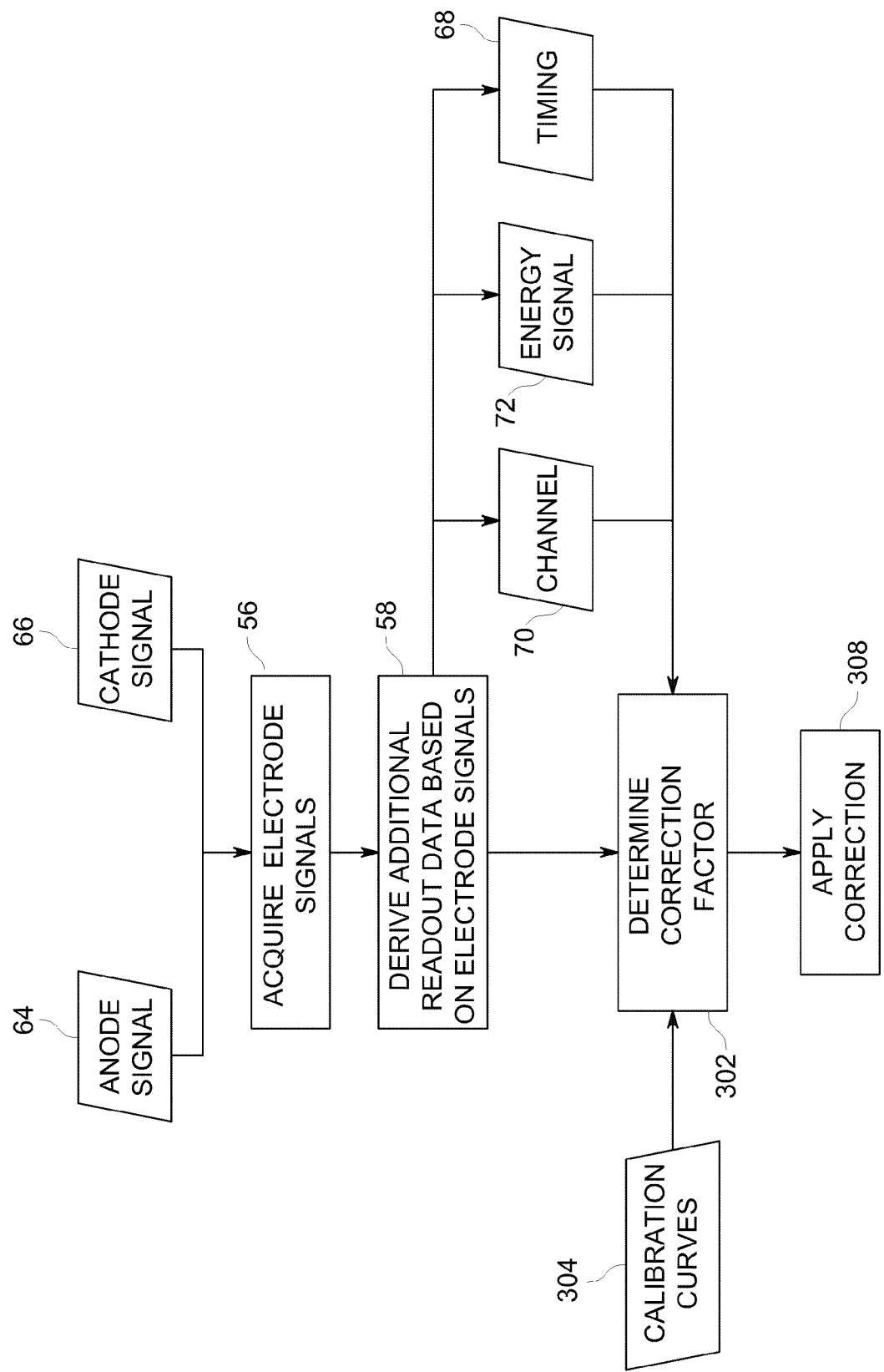
FIG. 22 is a flowchart depicting steps of an algorithm for applying a charge loss correction in accordance with aspects of the present disclosure.

The preceding describes various approaches for calculating a calibration factor or curve to address charge loss occurrence in an imaging system. FIG. 22 depicts a flowchart of an algorithm for applying such calibration data in an imaging operation. For example, in the accordance with this algorithm, data in the form of anode signals 64 and cathode signals 66 is acquired (block 56) during an examination or calibration session. Such read-out data may in turn be used to derive (block 58) additional data of interest, such as timing data 68, the anode, i.e., pixel, channel(s) 70, and/or the energy signal 72.

Based on the acquired and/or derived imaging data one or more correction factors may be determined (block 302) on the fly or by accessing stored calibration factors or curves 304, such as via a look-up table or other memory location. As will be appreciated, the stored calibration factors or curves 304 may be derived using the approaches discussed herein. Once the applicable correction factor is determined, the correction may be applied (block 308) to the acquired signal data to compensate or correct for charge losses in the detection process. The corrected or compensated signal data may then be used in subsequent processes for generating and displaying images based on the corrected data.

The preceding discussion provides examples and discussion of certain implementations by which calibration factors (e.g., correction offsets, multipliers, shifts, and so forth) may be determined to address charge loss in a detector. As will be appreciated, in certain embodiments such calibration factors may be determined once for a detector and subsequently used not just for that detector but for other detectors, such as for other detectors of the same model, having the same design, using the same materials, and so forth. That is, to the extent that depth/lateral corrections are a function of the basic physics of the device, the calibration relationship would only need to be determined once for devices having the same or similar structures. Thus, a calibration relationship determined for one detector may be used on other similar or identical detectors, such as by storing the derived calibration relationship in memories or tables accessible to the different detectors. Likewise, on-the-fly calculations of the type discussed herein may be performed on an ongoing or routine basis to confirm that such stored calibration relationships remain applicable to a given detector (i.e., to verify that the observed charge-loss remains consistent with the charge-loss relationship described by the stored calibration relationship). In instances where the stored calibration relationship is determined to be no longer valid, a new calibration relationship may be determined or accessed for the detector in question.

Further, for the sake of explanation the present discussion has described relationships as being determined for individual pixels and pairs of pixels. As will be appreciated, in certain embodiments where pixels can be grouped together with respect to location, performance, or other design factors, charge-loss corrections for such pixels (and comparisons using such pixels) may be based on the group or type of pixel in question. For example, pixels may be binned and processed as discussed herein based on row, column, whether the pixels are on edge of the detector, whether the pixels are at the center of the detector and so forth. In such embodiments, the corresponding calibration relationship (e.g., correction factors, offsets, and so forth) may be determined for the pixels in the respective groups. That is, the corresponding correction factors may be common across all pixels in a group or of a type.

Technical effects of the invention include restoring performance of a radiation detector, such as a CZT detector, by compensating for the occurrence of charge loss. Other technical effects of the invention include improving energy resolution and/or absolute count efficiency of a radiation detector.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for correcting for charge losses in a radiation detector, comprising the steps of:
    acquiring one or more anode signals and a cathode signal from the radiation detector, wherein the one or more anode signals and cathode signal arise in response to a gamma ray interaction with the radiation detector;
    determining a depth of interaction for the gamma ray interaction with the radiation detector;
    determining a lateral position of the gamma ray interaction with respect to the one or more anodes;
    sorting the one or more anode signals into one of a plurality of spectra based on the depth of interaction and lateral position;
    determining a correction factor based on the difference between the one or more anode signals and expected values for the one or more anode signals.

2. The method of claim 1, wherein the lateral position is determined with respect to a ratio of a first anode signal to a second anode signal.

3. The method of claim 2, wherein the difference comprises a difference between a mean value of the one or more anode signals and an expected mean value.

4. The method of claim 1, wherein the difference comprises a shift or offset between a peak fitted to an observed spectrum and one or more characteristic energy peaks.

5. The method of claim 1, wherein the plurality of spectra correspond to different lateral positions with respect to an anode electrode giving rise to at least one of the anode signals.

6. The method of claim 1, wherein determining the correction factor comprises one of determining an offset between the one or more anode signals and the expected values for the one or more anode signals, determining a ratio of mean peak height in a spectrum, or determining a multiplication factor for fitting expected and observed energy spectra.

7. The method of claim 1, wherein determining the depth of interaction comprises using a ratio of the cathode signal and anode signal to calculate the depth of interaction.

8. The method of claim 1, wherein determining the depth of interaction comprises using timing data to calculate the depth of interaction.

9. The method of claim 1, wherein the charge losses in the radiation detector comprise losses due to the charge being split between two or more anode electrodes such that a readout threshold of at least one of the anode electrodes is not exceeded and/or due to a portion of the charge not reaching the anodes during the integration time of the signal.

10. A method for determining a degree of signal loss at a radiation detector, comprising:
   determining a first subset of detected events in which radiation has interacted within a depth range less than the thickness of the radiation detector;
   determining a second subset of the detected events corresponding to lateral positions of the detected events within the radiation detector;
   generating a count profile for the frequency of occurrence of sums of a set of anode signals associated with the detected events; and
   based on the count profile, determining a fraction of signal lost for particular values of depth of interaction and lateral position.

11. The method of claim 10, comprising generating a calibration relationship for the radiation detector, wherein the calibration relationship can be used to correct for the fraction of signal lost at the radiation detector.

12. The method of claim 11, comprising storing the calibration relationship for use with a different radiation detector.

13. The method of claim 10, comprising accessing the calibration relationship when to determine one or more correction factors for signal data acquired using the radiation detector or a different radiation detector.

14. The method of claim 10, wherein determining the second subset of the detected events corresponding to lateral positions of the detected events within the radiation detector comprises sorting the detected events into radial categories based on where the detected events lie with respect to a plurality of lines that each describe a different respective ratio of a first pixel relative to a second pixel.

15. An imaging system, comprising:
   a radiation detector comprising a direct conversion material, one or more cathode electrodes disposed on a first surface of the direct conversion material, and a plurality of anode electrodes disposed on a second surface of the direct conversion material;
   data acquisition circuitry in communication with the one or more cathode electrodes and the plurality of anode electrodes;
   signal processing circuitry in communication with the data acquisition circuitry; and
   an operator workstation configured to control the operation of and to communicate with one or both of the data acquisition circuitry and the signal processing circuitry;
   wherein one or more of the data acquisition circuitry, the signal processing circuitry, or the operator workstation is configured to execute code which, when executed, performs the following:
     processes a measured set of signal data;
     accesses one or more correction factors suitable for correcting for charge loss as a result of being split between two or more of the anode electrodes or of being lost to a gap separating respective anode electrodes; and
     applies the one or more correction factors to the measured set of signal data to generate a corrected set of signal data corrected for the charge loss.

16. The imaging system of claim 15, wherein the direct conversion material comprises cadmium zinc telluride or other suitable semiconductors.

17. The imaging system of claim 15, wherein the one or more correction factors are accessed based on a depth of interaction and a lateral location for respective charge producing events within the radiation detector.

18. The imaging system of claim 15, wherein accessing the one or more correction factors comprises accessing a look-up table or other memory location where the correction factors are stored.

19. The imaging system of claim 15, wherein the one or more correction factors are derived from a calibration curve describing the charge loss expected based on depth of interaction and lateral orientation.

20. The imaging system of claim 15, wherein applying the one or more correction factors comprises adjusting some or all of the measured signal data to correspond to the amount of signal expected to be seen by the anode electrodes in the absence of charge loss.

* * * * *